(12) United States Patent
Ortoleva

(10) Patent No.: US 9,501,614 B2
(45) Date of Patent: Nov. 22, 2016

(54) METHOD FOR COMPUTER-AIDED VACCINE DISCOVERY

(71) Applicant: Indiana University Research and Technology Corp., Bloomington, IN (US)

(72) Inventor: Peter J. Ortoleva, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 683 days.

(21) Appl. No.: 13/900,079

(22) Filed: May 22, 2013

(65) Prior Publication Data

US 2013/0338988 A1    Dec. 19, 2013

Related U.S. Application Data

(60) Provisional application No. 61/649,953, filed on May 22, 2012.

(51) Int. Cl.
| | | |
|---|---|---|
| *G06G 7/58* | (2006.01) | |
| *G06F 19/16* | (2011.01) | |
| *G06F 19/12* | (2011.01) | |

(52) U.S. Cl.
CPC ............... *G06F 19/16* (2013.01); *G06F 19/12* (2013.01)

(58) Field of Classification Search
CPC ...................................................... G06F 19/16
USPC ............................................................ 703/11
See application file for complete search history.

(56) References Cited

PUBLICATIONS

Doytchinova et al. "The HLA-A2-supermotif: a QSAR definition" Org. Biomol. Chem. (2003) vol. 1, pp. 2648-2654.*
Cheluvaraja et al., "Thermal nanostructure: An order parameter multiscale ensemble approach", The Journal of Chemical Physics 132, 075102 (2010).
Joshi et al., "Epitope engineering and molecular metrics of immunogenicity: A computational approach to VLP-based vaccine design", Vaccine 31 (2013) 4841-4847.
Joshi et al., "A molecular dynamics study of loop fluctuation in human papillomavirus type 16 virus-like particles: A possible indicator of immunogenicity", Vaccine 29 (2011) 9423-9430.
Miao, et al., "Viral Structural Transition Mechanisms Revealed by Multiscale Molecular Dynamics/Order Parameter eXtrapolation Simulation", 2009 Wiley Periodicals, Inc., Biopolymers 93:61-73, 2010.
Singharoy et al., "Order parameters for macromolecules: Application to multiscale simulation", The Journal of Chemical Physics 134, 044104 (2011).
Singharoy et al., "Multiscale Macromolecular Simulation: Role of Evolving Ensembles", Journal of Chemical Information and Modeling 2012, 52, 2638-2649.

Aksimentiev A, Brunner R, Cohen J, Comer J, Cruz-Chu ER, Hardy D, et al. Computer Modeling in Biotechnology. A Partner in Development. Nanostructure Design Methods in Molecular Biology: SpringerLink; 2008. p. 181-234.
Amadei A, Linssen ABM, Berendsen HJC. Essential dynamics of proteins. Proteins: Struct Funct Bioinf. 1993;17(4):412-25.
Arkhipov A, Freddolino PL, Schulten K. Stability and Dynamics of Virus Capsids Described by Coarse-Grained Modeling. Structure. 2006;14(12):1767-77.
Berendsen, H.J.C., D. van der Spoel, and R. van Drunen, GROMACS: A message-passing parallel molecular dynamics implementation. Comput. Phys. Commun., 1995. 91(1-3): p. 43-56.
Bishop B, Dasgupta J, Klein M, Garcea RL, Christensen ND, Zhao R. Crystal Structures of Four Types of Human Papillomavirus L1 Capsid Proteins. J Biol Chem. 2007;282(43):31803-11.
Bishop B, Dasgupta J, Chen X. Structure-based engineering of papillomavirus major capsid L1: controlling particle assembly. Virology J. 2007;4:3.
Brown DR, Garland S, Ferris DG, Joura E, Steben M, James M, et al. The humoral response to GardasilTM over four years as defined by Total IgG and competitive Luminex immunoassay. Human Vaccines. 2011;7(2):230-8.
Cheluvaraja S, Ortoleva P. Thermal nanostructure: An Order Parameter/Multiscale Ensemble Approach. J Chem Phys. 2010;132(7):075102.
Chen, X.S., R.L. Garcea, I. Goldberg, G. Casini, and S.C. Harrison, Structure of Small Virus-like Particles Assembled from the L1 Protein of Human Papillomavirus 16. Mol. Cell, 2000. 5(3): p. 557-567.
Chi S-W, Maeng C-Y, Kim SJ, Oh MS, Ryu CJ, Kim S-J, et al. Broadly neutralizing anti-hepatitis B virus antibody reveals a complementarity determining region H3 lid-opening mechanism. Proc Natl Acad Sci. 2007;104:9230-5.
Cruz-Chu ER, Aksimentiev A, Schulten K. Water-Silica Force Field for Simulating Nanodevices. The Journal of Physical Chemistry B. 2006;110(43):21497-508.
Eisenhaber, F., P. Lijnzaad, P. Argos, C. Sander, and M. Scharf, The double cubic lattice method: Efficient approaches to numerical integration of surface area and volume and to dot surface contouring of molecular assemblies. Journal of Computational Chemistry, 1995. 16(3): p. 273-284.
Gohlke H, Thorpe MF. A Natural Coarse Graining for Simulating Large Biomolecular Motion. Biophys J. 2006;91(6):2115-20.
Guu, T.S.Y., Z. Liu, Q. Ye, D.A. Mata, K. Li, C. Yin, J. Zhang, and Y.J. Tao, Structure of the hepatitis E virus-like particle suggests mechanisms for virus assembly and receptor binding. Proc. Nat. Acad. Sci., 2009. 106(31): p. 12992-12997.

(Continued)

*Primary Examiner* — Jerry Lin
(74) *Attorney, Agent, or Firm* — Barnes & Thornburg LLP

(57) ABSTRACT

Virus-like particle (hereinafter sometimes VLP)-based strategies for developing vaccines against human viruses. Computer models of the VLPs are modified by the addition to the computer models of computer models of viral materials of the viruses against which the vaccines are being developed.

9 Claims, 6 Drawing Sheets

(56) References Cited

PUBLICATIONS

Humphrey, W., A. Dalke, and K. Schulten, VMD: Visual molecular dynamics. J. Mol. Graph., 1996. 14(1): p. 33-38.

Jaqaman K, Ortoleva PJ. New space warping method for the simulation of large-scale macromolecular conformational changes. J Comput Chem. 2002;23(4):484-91.

Jarymowycz LB, Ortoleva PJ. Involatile nanodroplets: an asymptotic analysis. J Chem Phys. 2006;124(23):234705 (4 pp.).

Joshi H, Cheluvaraja S, Somogyi E, Brown DR, Ortoleva PJ. A molecular dynamics study of loop fluctuation in human papillomavirus type 16 virus-like particles: a possible indicator of immunogenicity. Vaccine. 2011;29(51):9423-30.

Joshi H, Singharoy AB, Sereda YV, Cheluvaraja SC, Ortoleva PJ. Multiscale simulation of microbe structure and dynamics. Prog Biophys Mol Biol. 2011;107(1):200-17.

Lee, B. and F.M. Richards, The interpretation of protein structures: estimation of static accessibility. J Mol Biol, 1971. 55(3): p. 379-400.

Lentz, K., A. Smith, S. Geisler, S. Cox, P. Buontempo, A. Skelton, J. DeMartino, E. Rozhon, J. Schwartz, V. Girijavallabhan, J. O'Connell, and E. Arnold, Structure of poliovirus type 2 Lansing complexed with antiviral agent SCH48973: comparison of the structural and biological properties of three poliovirus serotypes. Structure, 1997. 5(7): p. 961-978.

Lindahl, E., B. Hess, and D.v.d. Spoel, GROMACS 3.0: A package for molecular simulation and trajectory analysis. J. Mol. Mod., 2001. 7: p. 306-317.

Maher M, Puget JF, Backofen R, editors. Constraint Techniques for Solving the Protein Structure Prediction Problem1998.

Marrink SJ, Risselada HJ, Yefimov S, Tieleman DP, de Vries AH. The Martini forcefield: coarse grained model for biomolecular simulations. J Phys Chem B. 2007;111:7812-24.

Miao Y, Johnson JE, Ortoleva PJ. All-Atom Multiscale Simulation of Cowpea Chlorotic Mottle Virus Capsid Swelling. J Phys Chem B. 2010;114(34):11181-95.

Miao Y, Ortoleva PJ. Molecular Dynamics/Order Parameter eXtrapolation (MD/OPX) for Bionanosystem Simulations. J Comput Chem. 2009;30(3):423-37.

Miao Y, Ortoleva PJ. Viral structural transitions: an all-atom multiscale theory. J Chem Phys. 2006;125(21):214901.

Modis Y, Trus BL, Harrison SC. Atomic model of the papillomavirus capsid. EMBO J. 2002;21(18):4754-62.

Monie A, Hung C-F, Roden R, Wu T-C. Cervarix™: a vaccine for the prevention of HPV 16, 18-associated cervical cancer. Biologics 2008;2(1):107-13.

Mount, D.W., Bioinformatics: Sequence and Genome Analysis2001, New York: Cold Spring Harbor Laboratory Press.

Nowak MA. Immune responses against multiple epitopes: a theory for immunodominance and antigenic variation. Seminars in Virology. 1996;7:83-92.

Ortoleva PJ, Iyengar S. Multiscale Theory of Collective and Single-Particle Modes in Quantum Nanosystem. J Chem Phys. 2008;128(16):164716.

Ortoleva PJ. Nanoparticle dynamics: A multiscale analysis of the Liouville equation. J Phys Chem B. 2005;109(45):21258-66.

Pankavich S, Shreif Z, Chen Y, Ortoleva PJ. Multiscale theory of finite size bose systems: Implications for collective and single-particle excitations. Phys Rev A. 2009;79(1):013628.

Pankavich S, Shreif Z, Ortoleva PJ. Multiscaling for Classical Nanosystems: Derivation of Smoluchowski and Fokker-Planck Equations. Physica A. 2008;387(16-17):4053-69.

Pankavich S, Shreif Z, Miao Y, Ortoleva PJ. Self-assembly of nanocomponents into composite structures: Derivation and simulation of Langevin equations J Chem Phys. 2009;130(19):194115-24.

Pankavich S, Miao Y, Ortoleva J, Shreif Z, Ortoleva PJ. Stochastic dynamics of bionanosystems: Multiscale analysis and specialized ensembles. J Chem Phys. 2008;128(23):234908-20.

Phillips JC, Braun R, Wang W, Gumbart J, Tajkhorshid E, Villa E, et al. Scalable molecular dynamics with NAMD. J Comput Chem. 2005;26(16):1781-802.

Press, W.H., B.P. Flannery, S.A. Teukolsky, and W.T. Vetterling, Numerical Recipes: The Art of Scientific Computing. 1987, Cambridge: Cambridge U. Press.

Riccardi L, Nguyen PH, Stock G. Free-Energy Landscape of RNA Hairpins Constructed via Dihedral Angle Principal Component Analysis. J Phys Chem B. 2009;113(52):16660.

Rice P, Longden I, Bleasby A. EMBOSS: The European Molecular Biology Open Software Suite. Trends in Genet. 2000;16(6):276-7.

Sadeyen J-Ré, Tourne S, Shkreli M, Sizaret P-Y, Coursaget P. Insertion of a foreign sequence on capsid surface loops of human papillomavirus type 16 virus-like particles reduces their capacity to induce neutralizing antibodies and delineates a conformational neutralizing epitope. Virology. 2003;309(1):32-40.
Schulz R, Lindner B, Petridis L, Smith JC. Scaling of Multimillion-Atom Biological Molecular Dynamics Simulation on a Petascale Supercomputer. J Chem Theor Comp. 2009;5(10):2798-808.
Shreif Z, Ortoleva PJ. Computer-Aided Design of Nanocapsules for Therapeutic Delivery. Comput Math Methods Med. 2009;10(1):49-70.
Shreif Z, Ortoleva P. Curvilinear All-Atom Multiscale (CAM) Theory of Macromolecular Dynamics. J Stat Phys. 2008;130(4):669-85.
Shreif Z, Adhangale P, Cheluvaraja S, Perera R, Kuhn RJ, Ortoleva PJ. Enveloped viruses understood via multiscale simulation: computer-aided vaccine design. Sci Model Simul. 2008;15(1-3):363-80.
Shreif Z, Pankavich S, Ortoleva PJ. Liquid-crystal transitions: A first-principles multiscale approach. Phys Rev E. 2009;80(3):031703.
Shreif Z, Ortoleva PJ. Multiscale Approach to Nanocapsule Design. Technical Proceedings of the 2008 NSTI Nanotechnology Conference and Trade Show. 2008;3:741-4.
Singharoy A, Sereda YV, Ortoleva PJ. Hierarchical Order Parameters for Macromolecular Assembly Simulations I: Construction and Dynamical Properties of Order Parameters. accepted to J Chem Theor Comput. 2012.
Singharoy A, Joshi H, Miao Y, Ortoleva P. Space Warping Order Parameters and Symmetry: Application to Multiscale Simulation of Macromolecular Assemblies. accepted to J Phys Chem. 2012.
Ayton et al., "Multiscale simulation of transmembrane proteins", Journal of Structural Biology 157 (2007) 570-578.
Grant et al., "Structures of poliovirus complexes with anti-viral drugs: implications for viral stability and drug design", Current Biology 1994, vol. 4 No. 9, 784-797.
Hayward et al., "Model-Free Methods of Analyzing Domain Motions in Proteins From Simulation: A Comparison of Normal Mode Analysis and Molecular Dynamics Simulation of Lysozyme", Proteins: Structure, Function, and Genetics 27:425-437 (1997).
Hayward et al., "Harmonicity and Anaharmonicity in Protein Dynamics: A Normal Mode Analysis and Principal Component Analysis", Proteins: Structure, Function, and Genetics 27:177-1867 (1995).
Maurice R. Hilleman, "Overview of the pathogenesis, prophylaxis and therapeusis of viral hepatitis B, with focus on reduction to practical applications", Vaccine 19 (2001) 1837-1848.
Klenin et al., "Derivatives of Molecular Surface Area and Volume: Simple and Exact Analytical Formulas", J. Comput Chem 32: 2647-2653, 2011.
MacKerell, Jr., et al., "Development and Current Ststus of the CHARMM Force Field for Nucleic Acids", Biopolymers (Nucleic Acid Sciences), vol. 56, 257-265 (2001).
Miller et al., "Ab initio Phasing of High-symmetry Macromolecular Complexes: Successful Phasing of Authentic Poliovirus Data to 3.0 A Resolution", J. Mol. Biol. (2001) 307, 499-512.
Ponder et al., "Force Fields for Protein Simulations", Advances in Protein Chemistry, vol. 66, 27-85, 2003.
Sette et al., "Epitope-based vaccines: an update on epitope identification, vaccine design and delivery", Current Opinion in Immunology 2003, 15:461-470.
Shrake et al., "Environment sand Exposure to Solvent of Protein Atoms, Lysozyme and Insulin", J. Mol. Biol. (1973) 79, 351-371.

(56) References Cited

OTHER PUBLICATIONS

Taufer et al., "Computational Multiscale Modeling in Protein-Ligand Docking", IEEE Engineering in Medicine and Biology Magazine, Mar./Apr. 2009, 28(2): 58-69.
Smith JF, Brownlow M, Brown M, Kowalski R, Esser MT, Wruiz W, et al. Antibodies from Women Immunized with Gardasil® Cross-Neutralize HPV 45 Pseudovirions. Human Vaccine. 2007;3(4):109-15.
Thönes N, Herreiner A, Schädlich L, Piuko K, Müller M. A Direct Comparison of Human Papillomavirus Type 16 L1 Particles Reveals a Lower Immunogenicity of Capsomeres than Viruslike Particles with Respect to the Induced Antibody Response J Virol. 2008;82(11):5472-85.
Uvarov A, Fritzsche S. Friction of N-bead macromolecules in solution: Effects of the bead-solvent interaction. Phys Rev E. 2006;73:011111.
Vanommeslaeghe K, Hatcher E, Acharya C, Kundu S, Zhong S, Shim J, et al. CHARMM general force field: A force field for drug-like molecules compatible with the CHARMM all-atom additive biological force fields. . J Comput Chem 2009;31(4):671-90.
Wang, X., W. Peng, J. Ren, Z. Hu, J. Xu, Z. Lou, X. Li, W. Yin, X. Shen, C. Porta, T.S. Walter, G. Evans, D. Axford, R. Owen, D.J. Rowlands, J. Wang, D.I. Stuart, E.E. Fry, and Z. Rao, A sensor-adaptor mechanism for enterovirus uncoating from structures of EV71. Nat. Struct. Mol. Biol., 2012. 19(4): p. 424-429.
Zhou J, Thorpe IF, Izvekov S, Voth GA. Coarse-Grained Peptide Modeling Using a Systematic Multiscale Approach. Biophys J. 2007;92(12):4289-303.
Cowan G., Statistical Data Analysis, 1998, Oxford University Press: New York.
Arkhipov A, Schulen K, Freddolino P, Ying Y, Shih A, Chen Z. Application of Residue-Based and Shape-Based Coarse-Graining to Biomolecular Simulations. Coarse-Graining of Condensed Phase and Biomolecular Systems: CRC Press; 2008. p. 299-315.
Weiser J, Shenkin P, and Still W, Approximate atomic surfaces form linear combinations of pairwise overlaps (LCPO). Journal of Computational Chemistry, 1999. 20(2): p. 217-230.
HPV and Cervical Cancer in the World 2007 Report; 2007 Contract No. Document Number.
Ortoleva, et al., "Hierarchical multiscale modeling of macromolecules and their assemblies", Soft Matter, 2013, 9, 4319-4335.
Singharoy et al., "Multiscale Macromolecular Simulation: Role of Evolving Ensembles", J. Chem. Inf. Model, 2012, 52, 2638-2649.

* cited by examiner

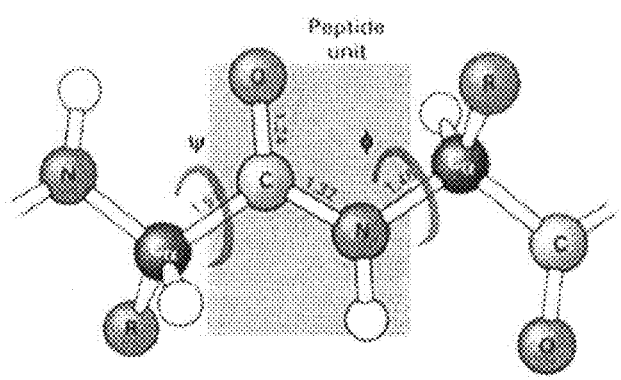
Figure 6. Definition of dihedral angles along the peptide backbone.

METHOD FOR COMPUTER-AIDED VACCINE DISCOVERY

CROSS REFERENCE TO RELATED APPLICATIONS

This application claims the benefit of the May 22, 2012 filing date of U.S. Ser. No. 61/649,953. The disclosure of U.S. Ser. No. 61/649,953 is hereby incorporated herein by reference.

SUMMARY

According to an aspect, a method for modeling virus-like particles (VLPs) that simultaneously captures VLP-wide and atomic-scale behaviors comprises testing the thermal stability of the VLP by determining the presence of the C-terminal helices of the L1 protein.

According to another aspect, a method for predicting immunogenicity comprises inputting deductive multiscale simulator (DMS) simulations to a formula relating the DMS simulations to immunogenicity to predict virus-like particle (VLP)-wide factors.

Illustratively, the method further comprises calibrating the formula using the thus-developed database on VLP structural stability and molecular metrics of a spectrum of VLPs.

Illustratively, the molecular metrics include at least one of epitope structure, epitope fluctuations, and the strength of binding to antibodies.

Illustratively, inputting DMS simulations to a formula relating them to immunogenicity to predict VLP-wide factors comprises developing a set of order parameters (OPs) characterized by at least one of the following: (1) Langevin equations that are force-field based; (2) forces that are constructed via on-the-fly ensemble methods, whose dependence on the OPs is not hypothesized using phenomenological expressions; (3) the OPs account for variations in time of both overall and atomic-scale features; (4) providing physics-based criteria to identify and dynamically construct missing OPs as needed in the course of a simulation; (5) the OPs capture symmetry breaking transitions; (6) computational efficiency at least an order of magnitude greater than that of conventional molecular dynamics (hereinafter sometimes MD).

According to another aspect, a method of designing a set of candidate vaccine virus-like particles (VLPs) comprises testing the immunogenicity of VLPs via at least one of vaccine computer-aided discovery (VCAD) and associated molecular-scale properties.

Illustratively, designing a set of candidate vaccine VLPs comprises designing a set of candidate vaccine VLPs having epitope behavior mimicking the behavior of the target virus.

Illustratively, designing a set of candidate vaccine VLPs comprises replacing at least one epitope of a VLP that is a successful vaccine for a second virus with at least one epitope of the target virus.

Illustratively, designing a set of candidate vaccine VLPs comprises dressing an inert nanocore with at least one epitope-bearing component of the target virus.

According to another aspect, a method for computationally synthesizing a virus-like particle (VLP) design strategy comprises constructing VLPs computationally and predicting their immunogenicity by connecting molecular scale metrics to immunogenicity via bioinformatics.

According to another aspect, a method for constructing and populating a vaccine computer-aided discovery (VCAD) database comprises archiving at least one of experimental and computationally derived information regarding at least one of viruses and virus-like particles (VLPs).

Illustratively, constructing and populating a VCAD database that archives experimental and computationally derived information regarding at least one of viruses and VLPs comprises constructing and populating a VCAD database that archives experimental and computationally derived information regarding at least one of structure, molecular metrics, and observed degrees of immunogenicity.

Illustratively, constructing and populating a VCAD database that archives experimental and computationally derived information regarding at least one of viruses and VLPs comprises running deductive multiscale simulator (DMS) software for each of a plurality of VLPs to obtain quantitative information on the molecular metrics of each of the plurality of VLPs.

Illustratively, constructing and populating a VCAD database that archives experimental and computationally derived information regarding at least one of viruses and VLPs comprises automatically analyzing a DMS simulation to extract molecular scale metrics.

Illustratively, automatically analyzing a DMS simulation to extract molecular scale metrics comprises automatically analyzing a DMS simulation via a computer program written in the python scripting language.

Illustratively, constructing and populating a VCAD database that archives experimental and computationally derived information regarding at least one of viruses and VLPs comprises constructing and populating a VCAD database via the relational database software MYSQL.

Illustratively, constructing and populating a VCAD database that archives experimental and computationally derived information regarding at least one of viruses and VLPs comprises archiving at least one of: structural data for the VLP or virus; structural data for an antibody of the VLP or virus; values of multiple molecular metrics obtained via DMS simulation; experimental information on immunogenicity; annotation on sources of information provided; and, DMS input files used to probe thermal stability or molecular metrics for the VLP or virus.

According to another aspect, a method for ranking the immunogenicity of virus-like particles (VLPs) comprises ranking VLPs according to at least one of: (1) overall VLP size; (2) overall VLP shape; (3) VLP thermal stability in blood or other fluids; (4) epitope peptide sequence; (5) epitope 3-dimensional conformation; (6) structures, relative to each other, of a set of closely located epitopes; (7) amplitude of epitope structural fluctuations; and, (8) strength of epitope binding to an antibody for the target virus.

Illustratively, ranking VLPs according to at least one of: (1) overall VLP size; (2) overall VLP shape; (3) VLP thermal stability in [blood or other] fluids; (4) epitope peptide sequence; (5) epitope 3-dimensional conformation; (6) structures, relative to each other, of a set of closely located epitopes; (7) amplitude of epitope structural fluctuations; and, (8) strength of epitope binding to an antibody for the target virus comprises constructing from the predicted time-course of the positions and momenta of all atoms in the VLP and its microenvironment M molecular metrics $\lambda_m$, each positive, with small $\lambda_m$ indicating high immunogenicity, defining for each metric $\lambda_m$ an immunogenicity factor $\mu_m$, calculating from the M immunogenicity factors $\{\mu_1, \mu_2, \ldots, \mu M\}$ an average value $\mu$, selecting a weight $w_m$ that expresses the expectation of the importance of each metric $\lambda_m$ relative to the other metrics $\lambda_{m'}$, calculating the immunogenicity based on all the available factors to arrive at an expected immunogenicity $\mu$ $$\mu = (\Sigma^* w_m)^{-1} \Sigma^* w_m \mu_m,$$

summing over all available m, with the * (asterisks) indicating that only contributions for metrics $\lambda_m$ that are available are included.

Illustratively, each $\mu_m = (1+x_m)^{-1}$ where $x_m = (a_m \lambda_m)^2$ for factor $a_m$ to be calibrated, $\mu_m$ near zero implying low likely immunogenicity, $\mu_m$ near 1 implying high likely immunogenicity, and $\mu_m$ near ½ implying marginal immunogenicity.

Illustratively, $\underline{a} = \{a_1, a_2, \ldots a_M\}$, $\underline{w} = \{w_1, w_2, \ldots w_M\}$, and $\underline{\lambda} = \{\lambda_1, \lambda_2, \ldots \lambda_M\}$, and the method further includes calibrating $\underline{a}$ and $\underline{w}$ using least squares fitting.

Illustratively, the method further includes randomly dividing the database of VLPs with experimentally known immunogenicity into two groups, one providing a second database and the other providing a first set of predictions for a set of VLPs of interest, comparing the first set of predictions and the second database, computing from this comparison a percent success in predicting immunogenicity; then randomly dividing the database of VLPs with experimentally known immunogenicity again into two groups, one providing a third database and the other providing a second set of predictions for a set of VLPs of interest, comparing the second set of predictions and the third database, computing from this comparison a second percent success in predicting immunogenicity; and, repeating this procedure with different random divisions of the data to obtain an estimate of overall success.

Illustratively, the method further comprises concluding that the database is adequate when further addition of new VLPs does not change $\underline{a}$ and $\underline{w}$ beyond arbitrary limits $\epsilon_{\underline{a}}$ and $\epsilon_{\underline{w}}$, respectively.

Illustratively, the method further includes obtaining a quantitative laboratory measure to provide a more quantitative calibration of the $\underline{a}$-dependence of $\lambda(\underline{\lambda}, \underline{a})$.

Illustratively, obtaining a quantitative laboratory measure comprises obtaining a quantitative laboratory measure of observed antibody counts.

According to another aspect, a method for validation of the immunogenicity of computationally generated virus-like particles (VLPs) comprises computationally generating the VLP, simulating the VLP via deductive multiscale simulator (DMS) software, and then predicting the immunogenicity for a target virus from the simulated information.

Illustratively, computationally generating the VLP comprises computationally generating at least one of human papillomavirus (HPV), poliovirus, and Hepatitis E (HEV).

Illustratively, computationally generating the VLP comprises including at least one epitope of a target virus on the VLP.

Illustratively, computationally generating the VLP comprises including at least one epitope of a target virus on at least one of HPV, poliovirus, and HEV.

According to another aspect, a method for validating computationally generated virus-like particle (VLP) immunogenicity comprises providing FDA approved silica nanocores (NCs), and binding epitope bearing proteins of a target virus to the NCs.

Illustratively, binding epitope bearing proteins of a target virus to the NCs comprises carrying out high-level quantum chemical calculations on model systems consisting of a relatively small moiety representing the NC, a $-(CH_2)_3$ $NH_2$ linker molecule and a small section of viral protein, then parametrizing the linker molecule, then increasing the complexity of the model while monitoring the changes of the force fields for convergence to a uniform value.

According to another aspect, a method for the computer-aided design of vaccines comprises using molecular simulation of a proposed vaccine nanoparticle to predict the proposed vaccine nanoparticle's overall and molecular scale properties, and applying bioinformatics to the thus-predicted properties to predict the likely immunogenicity of the proposed vaccine nanoparticle.

Illustratively, the thus-predicted properties include overall size, geometry and thermal stability of the proposed vaccine nanoparticle.

Illustratively, the thus-predicted properties include epitope conformation, the geometric relation between multiple closely-lying epitopes, and the statistics of the variations of epitope structure over time as predicted by the molecular simulation.

BRIEF DESCRIPTION OF THE DRAWINGS

The invention may best be understood by referring to the following detailed description and accompanying drawings which illustrate the invention. In the drawings:

FIG. 6 illustrates backbone dihedral angles for the epitope-bearing loop.

DETAILED DESCRIPTION

Figure 1C:
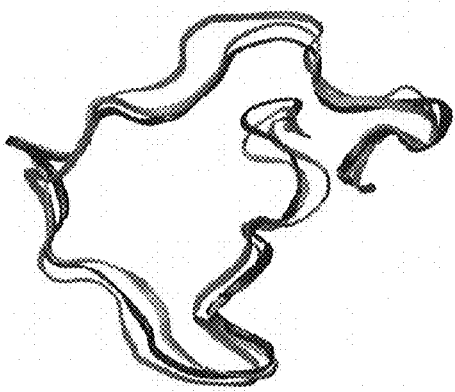
FIG. 1(c) illustrates that while epitope structure is similar in monomer (black), pentamer (red), and T=1 VLP (green) (suggested here via a measure of structural overlap), immunogenicity differences must come from another molecular scale characteristic, such as, for example, epitope fluctuation amplitude.
Figure 1B:
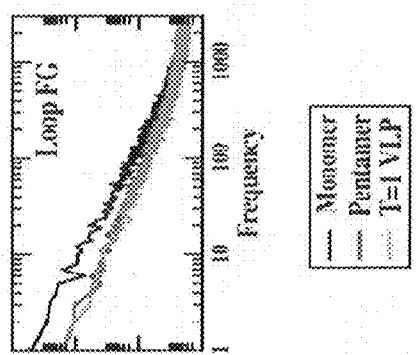
FIG. 1(b) illustrates the power spectrum of epitope structure fluctuation amplitude for three loops showing characteristics that distinguish between L1 monomer (black), L1 pentamer (red), and the full T=1 VLP (green)

A virus-like particle (hereinafter sometimes VLP)-based strategy has proven successful in developing a highly effective and safe vaccine against human papillomavirus (hereinafter sometimes HPV), the sole causative agent of cervical cancer, and a major cause of vaginal, vulvar, anal, oropharyngeal, penile, and other cancers. Two vaccines are approved for HPV. Thus, the synthetic VLP-based vaccine strategy is well-established. VLP-based vaccines against Hepatitis E and Chikungunya viruses are presently under development, indicating wider potential applicability of such vaccines. These VLPs are typically designed using traditional wet-laboratory-based approaches, involving mutation, assembly, and immunogenicity testing. The present invention is intended to enhance vaccine development via an efficient, cost-effective computer-aided design approach.

A highly efficient workflow for vaccine computer-aided discovery, (hereinafter sometimes VCAD) can be developed by integrating advanced nanoparticle simulation, bioinformatics, standard nanoparticle synthesis methods, and traditional laboratory immunogenicity testing. The disclosed advanced nanoparticle simulation approach has already been implemented as the deductive multiscale simulator (hereinafter sometimes DMS) software. By way of background, the DMS software performs an 11-step process that works as follows:

1. Propose VLP structural concept (i.e., a capsid of one virus with epitopes of the target virus).
2. Make all-atom structural model using conventional molecular modeling tools.

3. Run simulation to assess stability and interaction with cell surface and bloodstream using multiscale, physics-based modeling software that accounts for the motion of all the atoms involved and the forces between them.

4. Use physics-based molecular simulation of the VLP; Use results to derive information on structure and other properties of key epitopes delivered by the VLP.

5. Perform bioinformatics computations using VCAD database on metrics for VLPs to estimate likely immunogenicity for the target virus; the database contains information on VLPs of known immunogenicity to enable this assessment.

6. Arrive at assessment of likely immunogenicity for target virus using results of step 5.

7. Perform simulation of self-assembly to arrive at synthesis strategy using multiscale or conventional molecular dynamics computational platform.

8. Synthesize VLPs using self-assembly pathway identified computationally in step 7.

9. Perform wet laboratory assessment of thermal stability of synthesized VLPs.

10. Perform laboratory tests, i.e., pseudovirion neutralization assays and/or animal studies.

11. Design clinical trials.

The informatics facet of the VCAD approach is explored here.

The proposed informatics approach uses a database that relates experimentally observed immunogenicity to molecular scale DMS-generated information on known successful and unsuccessful VLP vaccines. This database is used to calibrate a postulated relationship between immunogenicity and molecular scale properties. This calibrated relationship is then used to assess the immunogenicity of a candidate VLP vaccine from its molecular scale information. After repeating this procedure for a set of candidate VLPs, the most promising candidates are synthesized and evaluated via pseudovirion neutralization or other assays.

Here, two VLP constructs are used to validate the VCAD approach. The two VLP constructs are designed to present regions (called epitopes) of proteins on a viral surface. Epitopes are protein loops read by the immune system on the surface of a pathogen. In the first, the VLP used in the HPV vaccine is modified by computationally inserting epitopes of a different target virus. In the second, an inert nanocore is dressed with epitopes of the target virus.

In this investigation, the immunogenicity prediction step of workflow is enabled by achieving the following specific aims: first, to construct and populate a VCAD database used to calibrate the immunogenicity-prediction formula; second, to calibrate and validate an immunogenicity-prediction formula that takes molecular metrics predicted via a simulator and yields a likelihood of immunogenicity for the target virus using information in the VCAD database; and, third, to validate the immunogenicity prediction approach using data on HPV, poliovirus and hepatitis E by determining the accuracy of immunogenicity predictions for the three test systems.

§I. Significance

A vaccine discovery workflow is developed. Software for simulating a vaccine nanoparticle simulation has already been developed and validated. See, for example: Singharoy A, Joshi H, Miao Y, Ortoleva P. Space Warping Order Parameters and Symmetry: Application to Multiscale Simulation of Macromolecular Assemblies. accepted to J Phys Chem. 2012; Singharoy A, Sereda Y V, Ortoleva P J. Hierarchical Order Parameters for Macromolecular Assembly Simulations I: Construction and Dynamical Properties of Order Parameters. accepted to J Chem Theor Comput. 2012; Singharoy A, Joshi H, Ortoleva P J. History sampling accelerated multiscale bionanosystem: bionanosystem simulation. In preparation. 2012; Singharoy A, Cheluvaraja S, Ortoleva P J. Order parameters for macromolecules: Application to multiscale simulation. J Chem Phys. 2011; 134: 044104; Joshi H, Singharoy A B, Sereda Y V, Cheluvaraja S C, Ortoleva P J. Multiscale simulation of microbe structure and dynamics. Prog Biophys Mol Biol. 2011; 107(1):200-17; Miao Y, Ortoleva P J. Viral Structural Transition Mechanisms Revealed by Multiscale Molecular Dynamics/Order Parameter eXtrapolation Simulation Biopolymers. 2010; 93(1):61-73; Cheluvaraja S, Ortoleva P. Thermal nanostructure: An Order Parameter/Multiscale Ensemble Approach. J Chem Phys. 2010; 132(7):075102; Pankavich S, Shreif Z, Miao Y, Ortoleva P J. Self-assembly of nanocomponents into composite structures: Derivation and simulation of Langevin equations J Chem Phys. 2009; 130(19):194115-24; Miao Y, Ortoleva P J. Molecular Dynamics/Order Parameter eXtrapolation (MD/OPX) for Bionanosystem Simulations. J Comput Chem. 2009; 30(3):423-37; and, Pankavich S, Shreif Z, Ortoleva P J. Multiscaling for Classical Nanosystems: Derivation of Smoluchowski and Fokker-Planck Equations. Physica A. 2008; 387(16-17):4053-69.

The relationship between the output of such simulations and the immunogenicity of the nanoparticle.

Next, this approach is utilized to identify promising vaccine nanoparticles for specified viruses, synthesize them in the laboratory, and test their immunogenicity experimentally. The types of vaccines considered are based on VLPs that do not contain genetic material. This avoids the danger of unforeseen proliferation. Using genome-free VLPs as the basis of antiviral vaccines is already in practice (e.g., Gardasil® and Cervarix® against HPV; see, for example; Brown D R, Garland S, Ferris D G, Joura E, Steben M, James M, et al. The humoral response to Gardasil™ over four years as defined by Total IgG and competitive Luminex immunoassay. Human Vaccines. 2011; 7(2):230-8; and, Monie A, Hung C-F, Roden R, Wu T-C. Cervarix™: a vaccine for the prevention of HPV 16, 18-associated cervical cancer. Biologics 2008; 2(1):107-13), or are in clinical trials (e.g., Hepatitis E VLP; see, for example, Guua T S Y, Liub Z, Yea Q, Mataa D A, Lic K, Yinb C, et al. Structure of the hepatitis E virus-like particle suggests mechanisms for virus assembly and receptor binding. Proc Natl Acad Sci. 2009; 106(31):12992-7), and Hepatitis B VLP (see, for example, Hilleman M. Overview of the pathogenesis, prophylaxis and therapeusis of viral hepatitis B, with focus on reduction to practical applications. Vaccine. 2001; 19(15-16):1837-48).

Vaccines are now designed using traditional wet-laboratory based approaches, involving mutation, assembly, and immunogenicity testing. With the present invention, these costly procedures are accelerated through computational steps including VLP simulation and immunogenicity prediction. Additional efficiencies are obtained through novel VLP designs that enable cell-free synthesis approaches. This disclosure develops VCAD for designing a vaccine against a given target virus.

A virus is an assembly of $10^5$ to $10^9$ atoms organized into proteins and RNA or DNA. The immune system responds to viral incursions by generating antibodies that reflect the specific arrangement and bonding among the atoms constituting the virus. The approach of the present disclosure is built on an atom-resolved physical and computational model. Interactions among atoms are now well-characterized by interatomic forces captured in available force fields (e.g., CHARMM; see, for example: MacKerell J A D, Banavali N, Foloppe N. Development and current status of the CHARMM force field for nucleic acids. Biopolymers. 2001; 56(4):257-65; and, Vanommeslaeghe K, Hatcher E, Acharya C, Kundu S, Zhong S, Shim J, et al. CHARMM general force field: A force field for drug-like molecules compatible with the CHARMM all-atom additive biological force fields. J Comput Chem 2009; 31(4):671-90), or AMBER (see, for example, Ponder J W, Case D A. Force fields for protein simulations. Advances in Protein Chemistry 2003; 66:27-85). Since it is based on an all-atom model and these force fields, the disclosed approach avoids the need of extensive laboratory data for calibration and its associated costs.

An all-atom formulation presents a challenge for computer simulations. However, the disclosed mathematical and computational approach (§II. A) addresses this challenge. The gap between predicting the atom-resolved structure of a virus or VLP versus predicting the response of the immune system is bridged via a novel immunogenicity informatics approach (§II. B). This approach uses a database of quantitative structural information on nanoparticles, each known to be immunogenic or non-immunogenic for a variety of viruses. Integrating these elements promotes efficiency and cost-saving in vaccine discovery.

As a specific example of a VLP-based vaccine, consider Gardasil®, a vaccine against human papillomavirus (HPV), the causative agent of cervical cancer (see, for example: Brown D R, Garland S, Ferris D G, Joura E, Steben M, James M, et al. The humoral response to Gardasil® over four years as defined by Total IgG and competitive Luminex immunoassay. Human Vaccines. 2011; 7(2):230-8; and, Smith J F, Brownlow M, Brown M, Kowalski R, Esser M T, Wruiz W, et al. Antibodies from Women Immunized with Gardasil® Cross-Neutralize HPV 45 Pseudovirions. Human Vaccine. 2007; 3(4):109-15). The principal investigator (DR Brown) made major contributions to the development of Gardasil®. This vaccine yields protection from HPV types 16 and 18, which cause nearly 80% of all cervical cancers. The active ingredient in this vaccine is a VLP of 360 µl HPV capsid proteins assembled into an icosahedral structure (see, for example, Modis Y, Trus B L, Harrison S C. Atomic model of the papillomavirus capsid. EMBO J. 2002; 21(18): 4754-62). Gardasil® is expensive to synthesize and is temperature-sensitive, thereby limiting its use in third world countries where several hundred thousand women die annually from cervical cancer (see, for example, HPV and Cervical Cancer in the World 2007 Report; 2007 Contract No.: Document Number). The disclosed method enables in-silico design of VLPs with enhanced thermochemical stability.

The HPV vaccine nanoparticle and its immediate aqueous environment involve about 20 million atoms. Its dynamics involve processes acting on a wide range of spatial scales. Capturing interactions among the constituent atoms across these scales make all-atom VLP simulation and immunogenicity analysis a challenge (see, for example, Schulz R, Lindner B, Petridis L, Smith J C. Scaling of Multimillion-Atom Biological Molecular Dynamics Simulation on a Petascale Supercomputer. J Chem Theor Comp. 2009; 5(10): 2798-808). Understanding the atomic scale is needed to assess the interaction of a VLP with its microenvironment, and ultimately with the immune system, all of which are necessary for predicting the thermal stability and immunogenicity of a proposed VLP-based vaccine. To arrive at a computer-aided design workflow, many simulations of such large systems are required.

To address this, computational techniques have been developed which enable accurate, rapid, all-atom, long-time whole VLP simulations (see, for example: Singharoy A, Joshi H, Miao Y, Ortoleva P. Space Warping Order Parameters and Symmetry: Application to Multiscale Simulation of Macromolecular Assemblies. accepted to J Phys Chem. 2012; Singharoy A, Sereda Y V, Ortoleva P J. Hierarchical Order Parameters for Macromolecular Assembly Simulations I: Construction and Dynamical Properties of Order Parameters. accepted to J Chem Theor Comput. 2012; Singharoy A, Joshi H, Ortoleva P J. History sampling accelerated multiscale bionanosystem: bionanosystem simulation. In preparation. 2012; Singharoy A, Cheluvaraja S, Ortoleva P J. Order parameters for macromolecules: Application to multiscale simulation. J Chem Phys. 2011; 134: 044104; Joshi H, Singharoy A B, Sereda Y V, Cheluvaraja S C, Ortoleva P J. Multiscale simulation of microbe structure and dynamics. Prog Biophys Mol Biol. 2011; 107(1):200-17; Miao Y, Ortoleva P J. Viral Structural Transition Mechanisms Revealed by Multiscale Molecular Dynamics/Order Parameter eXtrapolation Simulation Biopolymers. 2010; 93(1):61-73; Cheluvaraja S, Ortoleva P. Thermal nanostructure: An Order Parameter/Multiscale Ensemble Approach. J Chem Phys. 2010; 132(7):075102; Pankavich S, Shreif Z, Miao Y, Ortoleva P J. Self-assembly of nanocomponents into composite structures: Derivation and simulation of Langevin equations J Chem Phys. 2009; 130(19):194115-24; Miao Y, Ortoleva P J. Molecular Dynamics/Order Parameter eXtrapolation (MD/OPX) for Bionanosystem Simulations. J Comput Chem. 2009; 30(3):423-37; and, Pankavich S, Shreif Z, Ortoleva P J. Multiscaling for Classical Nanosystems: Derivation of Smoluchowski and Fokker-Planck Equations. Physica A. 2008; 387(16-17):4053-69). This approach has been implemented as the DMS VLP simulator used in the disclosed computer-aided vaccine design strategy.

Figure 1A:
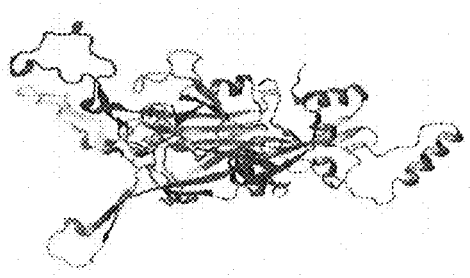
FIG. 1(a) illustrates the structure of L1 HPV 16 monomer with highlighted epitope regions.

HPV illustrates the subtleties in VLP design. The immune system senses epitopes and responds to them by generating specific antibodies that build in the information contained in these epitopes. For HPV, many epitopes are a part of the L1 capsid protein (FIG. 1(a)) that forms the HPV's outer coating (see, for example, Bishop B, Dasgupta J, Klein M, Garcea R L, Christensen N D, Zhao R. Crystal Structures of Four Types of Human Papillomavirus L1 Capsid Proteins. J Biol Chem. 2007; 282(43):31803-11). The immune response is believed to reflect one or several molecular metrics characterizing the epitopes: peptide sequence, loop conformation (FIG. 1(c)), or proximity and relative conformation of neighboring loops simultaneously (see, for example: Sette A, Fikes J. Epitope-based vaccines: an update on epitope identification, vaccine design and delivery Current Opinion in Immunology. 2003; 15(4):461-70; and, Nowak M A. Immune responses against multiple epitopes: a theory for immunodominance and antigenic variation. Seminars in Virology. 1996; 7:83-92). At first sight, this seems to imply that an L1 protein monomer or pentamer could serve as a vaccine, and thus VCAD would only require simulation of one or a few protein loops and their immediate environment. However, the monomer is not immunogenic and the pentamer is only modestly so, while the whole icosahedral VLP structure is highly immunogenic. See, for example, Thones N, Herreiner A, Schadlich L, Piuko K, Müller M. A Direct Comparison of Human Papillomavirus Type 16 µl Particles Reveals a Lower Immunogenicity of Capsomeres than Viruslike Particles with Respect to the Induced Antibody Response J. Virol. 2008; 82(11):5472-85. To investigate these subtle effects, the dynamical behavior of the important FG epitope loop of L1 protein monomer, pentamer, and VLP was studied. Average epitope geometry is similar across the monomer, pentamer, and VLP (FIG. 1(c)). In all these cases, the FG loop structure fluctuates in time. However, the time-average configuration is maintained across these structures (FIG. 1(c)). The root-mean-square (RMS) structural fluctuations for the three cases were also studied. RMS structural fluctuation decreases as the size of the structure increases. See, for example, Joshi H, Cheluvaraja S, Somogyi E, Brown D R, Ortoleva P J. A molecular dynamics study of loop fluctuation in human papillomavirus type 16 viruslike particles: a possible indicator of immunogenicity. Vaccine. 2011; 29(51):9423-30. Furthermore, this time-average RMS fluctuation amplitude was significant, i.e., it was greater than the structural differences among the three cases. This suggests that fluctuation intensity can be a more reliable indicator of immunogenicity than epitope structure. This observation is the basis of the fluctuation-immunogenicity hypothesis described in this disclosure. Thus, epitope structural fluctuation is one of the molecular properties used in the VLP immunogenicity prediction algorithm developed herein. This hypothesis provides guidance for designing novel VLPs whose stability and immunogenicity is then evaluated via VCAD.

The above considerations suggest that immunogenicity can be a VLP-wide effect as follows. The structure and fluctuation of epitopes in a given L1 protein can be strongly influenced by the proximity of neighboring proteins and the consequent interaction with the multiple-protein assembly. Thus, the VCAD approach involves whole VLP simulations to capture epitope average structure and fluctuation intensity.

The relationship between the output of DMS simulations and the immunogenicity of a VLP is developed. This integrated VCAD approach is then used to identify promising VLPs for specified viruses, synthesize them in the laboratory, and test their immunogenicity experimentally. A short list of vaccines against a specific virus is then created preparatory to clinical trials.

§II. A VLP Simulation Methodology

A VLP modeling approach that simultaneously captures VLP-wide and atomic-scale behaviors has been developed. See, for example: Miao Y, Ortoleva P J. Molecular Dynamics/Order Parameter eXtrapolation (MD/OPX) for Bionanosystem Simulations. J Comput Chem. 2009; 30(3):423-37; Pankavich S, Shreif Z, Ortoleva P J. Multiscaling for Classical Nanosystems: Derivation of Smoluchowski and Fokker-Planck Equations. Physica A. 2008; 387(16-17):4053-69; Brown D R, Garland S, Ferris D G, Joura E, Steben M, James M, et al. The humoral response to Gardasil® over four years as defined by Total IgG and competitive Luminex immunoassay. Human Vaccines. 2011; 7(2):230-8; Monie A, Hung C-F, Roden R, Wu T-C. Cervarix™: a vaccine for the prevention of HPV 16, 18-associated cervical cancer. Biologics 2008; 2(1):107-13; and, Guua T S Y, Liub Z, Yea Q, Mataa D A, Lic K, Yinb C, et al. Structure of the hepatitis E virus-like particle suggests mechanisms for virus assembly and receptor binding. Proc Natl Acad Sci. 2009; 106 (31):12992-7. To simulate VLP-wide structure, a set of variables has been developed. These variables are called order parameters (hereinafter sometimes OPs). These OPs capture supra nanometer-scale features. See, for example: Miao Y, Ortoleva P J. Viral Structural Transition Mechanisms Revealed by Multiscale Molecular Dynamics/Order Parameter eXtrapolation Simulation Biopolymers. 2010; 93(1):61-73; Ortoleva P J. Nanoparticle dynamics: A multiscale analysis of the Liouville equation. J Phys Chem B. 2005; 109(45):21258-66; Jarymowycz L B, Ortoleva P J. Involatile nanodroplets: an asymptotic analysis. J Chem Phys. 2006; 124(23):234705 (4 pp.); Miao Y, Ortoleva P J. Viral structural transitions: an all-atom multiscale theory. J Chem Phys. 2006; 125(21):214901; Ortoleva P J, Iyengar S. Multiscale Theory of Collective and Single-Particle Modes in Quantum Nanosystem. J Chem Phys. 2008; 128(16): 164716; Shreif Z, Adhangale P, Cheluvaraja S, Perera R, Kuhn R J, Ortoleva P J. Enveloped viruses understood via multiscale simulation: computer-aided vaccine design. Sci Model Simul. 2008; 15(1-3):363-80; Shreif Z, Ortoleva P. Curvilinear All-Atom Multiscale (CAM) Theory of Macromolecular Dynamics. J Stat Phys. 2008; 130(4):669-85; Shreif Z, Ortoleva P J. Multiscale Approach to Nanocapsule Design. Technical Proceedings of the 2008 NSTI Nanotechnology Conference and Trade Show. 2008; 3:741-4; Pankavich S, Shreif Z, Chen Y, Ortoleva P J. Multiscale theory of finite size bose systems: Implications for collective and single-particle excitations. Phys Rev A. 2009; 79(1):013628; Shreif Z, Ortoleva P J. Computer-Aided Design of Nanocapsules for Therapeutic Delivery. Comput Math Methods Med. 2009; 10(1):49-70; Shreif Z, Pankavich S, Ortoleva P J. Liquid-crystal transitions: A first-principles multiscale approach. Phys Rev E. 2009; 80(3):031703; and, Pankavich S, Ortoleva P. Multiscale Theory of soft matter. In preparation. 2010.

Novel techniques in statistical mechanics are used to derive equations governing the co-evolution of these OPs and the statistics of the atom-resolved state. See, for example: Singharoy A, Cheluvaraja S, Ortoleva P J. Order parameters for macromolecules: Application to multiscale simulation. J Chem Phys. 2011; 134:044104; Miao Y, Ortoleva P J. Viral Structural Transition Mechanisms Revealed by Multiscale Molecular Dynamics/Order Parameter eXtrapolation Simulation Biopolymers. 2010; 93(1):61-73; Cheluvaraja S, Ortoleva P. Thermal nanostructure: An Order Parameter/Multiscale Ensemble Approach. J Chem Phys. 2010; 132(7):075102; Miao Y, Johnson J E, Ortoleva P J. All-Atom Multiscale Simulation of Cowpea Chlorotic Mottle Virus Capsid Swelling. J Phys Chem B. 2010; 114(34):11181-95; and, Pankavich S, Miao Y, Ortoleva J, Shreif Z, Ortoleva P J. Stochastic dynamics of bionanosystems: Multiscale analysis and specialized ensembles. J Chem Phys. 2008; 128(23):234908-20. The latter statistics are then used to construct factors in the equations governing OP dynamics.

This OP-atomistic state interplay avoids the need for hypothesizing equations governing OP behavior and calibrating them. See, for example: Singharoy A, Joshi H, Miao Y, Ortoleva P. Space Warping Order Parameters and Symmetry: Application to Multiscale Simulation of Macromolecular Assemblies. accepted to J Phys Chem. 2012; Singharoy A, Sereda Y V, Ortoleva P J. Hierarchical Order Parameters for Macromolecular Assembly Simulations I: Construction and Dynamical Properties of Order Parameters. accepted to J Chem Theor Comput. 2012; Singharoy A, Joshi H, Ortoleva P J. History sampling accelerated multiscale bionanosystem: bionanosystem simulation. In preparation. 2012; Singharoy A, Cheluvaraja S, Ortoleva P J. Order parameters for macromolecules: Application to multiscale simulation. J Chem Phys. 2011; 134:044104; Joshi H, Singharoy A B, Sereda Y V, Cheluvaraja S C, Ortoleva P J. Multiscale simulation of microbe structure and dynamics. Prog Biophys Mol Biol. 2011; 107(1):200-17; Miao Y, Ortoleva P J. Viral Structural Transition Mechanisms Revealed by Multiscale Molecular Dynamics/Order Parameter eXtrapolation Simulation Biopolymers. 2010; 93(1):61-73; Cheluvaraja S, Ortoleva P. Thermal nanostructure: An Order Parameter/Multiscale Ensemble Approach. J Chem Phys. 2010; 132(7):075102; Pankavich S, Shreif Z, Miao Y, Ortoleva P J. Self-assembly of nanocomponents into composite structures: Derivation and simulation of Langevin equations J Chem Phys. 2009; 130(19):194115-24; Miao Y, Ortoleva P J. Molecular Dynamics/Order Parameter eXtrapolation (MD/OPX) for Bionanosystem Simulations. J Comput Chem. 2009; 30(3):423-37; and, Pankavich S, Shreif Z, Ortoleva P J. Multiscaling for Classical Nanosystems: Derivation of Smoluchowski and Fokker-Planck Equations. Physica A. 2008; 387(16-17):4053-69. This algorithm was implemented as the software package DMS.

Other software for simulating many-atom systems and their strength and limitations in the context of bionanosystem simulations have been discussed previously. See, for example: Shreif Z, Ortoleva P. Curvilinear All-Atom Multiscale (CAM) Theory of Macromolecular Dynamics. J Stat Phys. 2008; 130(4):669-85; Marrink S J, Risselada H J, Yefimov S, Tieleman D P, de Vries A H. The MARTINI forcefield: coarse grained model for biomolecular simulations. J Phys Chem B. 2007; 111:7812-24; Uvarov A, Fritzsche S. Friction of N-bead macromolecules in solution: Effects of the bead-solvent interaction. Phys Rev E. 2006; 73:011111; Arkhipov A, Schulten K, Freddolino P, Ying Y, Shih A, Chen Z. Application of Residue-Based and Shape-Based Coarse-Graining to Biomolecular Simulations. Coarse-Graining of Condensed Phase and Biomolecular Systems: CRC Press; 2008. p. 299-315; Gohlke H, Thorpe M F. A Natural Coarse Graining for Simulating Large Biomolecular Motion. Biophys J. 2006; 91(6):2115-20; Maher M, Puget J F, Backofen R, editors. Constraint Techniques for Solving the Protein Structure Prediction Problem 1998; Hayward S, Kitao A, Berendsen H J C. Model-free methods of analyzing domain motions in proteins from simulation: A comparison of normal mode analysis and molecular dynamics simulation of lysozyme. Proteins: Struct Funct Bioinf. 1997; 27(3):425-37; Hayward S, Kitao A, GO N. Harmonicity and anharmonicity in protein dynamics: A normal mode analysis and principal component analysis. Proteins: Struct Funct Bioinf. 1995; 23(2):177-86; Amadei A, Linssen A B M, Berendsen H J C. Essential dynamics of proteins. Proteins: Struct Funct Bioinf. 1993; 17(4):412-25; Zhou J, Thorpe I F, Izvekov S, Voth G A. Coarse-Grained Peptide Modeling Using a Systematic Multiscale Approach. Biophys J. 2007; 92(12):4289-303; Taufer M, Armen R S, Chen J, Teller P J, Brooks III C L. Computational Multi-Scale Modeling in Protein-Ligand Docking. IEEE Engineering in Medicine and Biology Magazine 2009. 2009; 28(2): 58-69; Ayton G S, Voth G A. Multiscale simulation of transmembrane proteins. J Struct Biol. 2007; 157(3):570-8; Riccardi L, Nguyen P H, Stock G. Free-Energy Landscape of RNA Hairpins Constructed via Dihedral Angle Principal Component Analysis. J Phys Chem B. 2009; 113(52):16660; and, Arkhipov A, Freddolino P L, Schulten K. Stability and Dynamics of Virus Capsids Described by Coarse-Grained Modeling. Structure. 2006; 14(12):1767-77. See also, for example, Joshi H, Singharoy A B, Sereda Y V, Cheluvaraja S C, Ortoleva P J. Multiscale simulation of microbe structure and dynamics. Prog Biophys Mol Biol. 2011; 107(1):200-17.

DMS has the following features relevant to vaccine design:

(1) Langevin equations governing the OP dynamics are force-field based. Thus all factors, such as, for example, thermal average forces and diffusivities, in these equations are computed "on-the-fly" from atomic forces and velocities. See, for example: Singharoy A, Cheluvaraja S, Ortoleva P J. Order parameters for macromolecules: Application to multiscale simulation. J Chem Phys. 2011; 134:044104; Cheluvaraja S, Ortoleva P. Thermal nanostructure: An Order Parameter/Multiscale Ensemble Approach. J Chem Phys. 2010; 132(7):075102; Ortoleva P J. Nanoparticle dynamics: A multiscale analysis of the Liouville equation. J Phys Chem B. 2005; 109(45):21258-66; and, Pankavich S, Miao Y, Ortoleva J, Shreif Z, Ortoleva P J.

Stochastic dynamics of bionanosystems: Multiscale analysis and specialized ensembles. J Chem Phys. 2008; 128(23): 234908-20.

(2) Forces driving OP dynamics are constructed via on-the-fly ensemble methods, and their dependence on the OPs need not be hypothesized using phenomenological expressions. In this way, DMS is applicable to a wide range of VLPs and conditions.

(3) The method accounts for the variations in time of both overall and atomic-scale features, as validated via comparison with conventional molecular dynamics (hereinafter sometimes MD) and VLP experimental data. See, for example: Singharoy A, Cheluvaraja S, Ortoleva P J. Order parameters for macromolecules: Application to multiscale simulation. J Chem Phys. 2011; 134:044104; Joshi H, Singharoy A B, Sereda Y V, Cheluvaraja S C, Ortoleva P J. Multiscale simulation of microbe structure and dynamics. Prog Biophys Mol Biol. 2011; 107(1):200-17; Cheluvaraja S, Ortoleva P. Thermal nanostructure: An Order Parameter/ Multiscale Ensemble Approach. J Chem Phys. 2010; 132 (7):075102; Ortoleva P J. Nanoparticle dynamics: A multiscale analysis of the Liouville equation. J Phys Chem B. 2005; 109(45):21258-66; and, Pankavich S, Miao Y, Ortoleva J, Shreif Z, Ortoleva P J. Stochastic dynamics of bionanosystems: Multiscale analysis and specialized ensembles. J Chem Phys. 2008; 128(23):234908-20.

(4) Physics-based criteria are provided to identify and dynamically construct missing OPs as needed in the course of a simulation. See, for example, Singharoy A, Cheluvaraja S, Ortoleva P J. Order parameters for macromolecules: Application to multiscale simulation. J Chem Phys. 2011; 134:044104.

(5) Symmetry breaking transitions (e.g., disassembly of icosahedral structures) are captured. See, for example: Miao Y, Ortoleva P J. Viral Structural Transition Mechanisms Revealed by Multiscale Molecular Dynamics/Order Parameter eXtrapolation Simulation Biopolymers. 2010; 93(1):61-73; and, Miao Y, Johnson J E, Ortoleva P J. All-Atom Multiscale Simulation of Cowpea Chlorotic Mottle Virus Capsid Swelling. J Phys Chem B. 2010; 114(34):11181-95).

(6) The computational efficiency of DMS is orders of magnitude greater than that of conventional MD, making DMS uniquely suited for vaccine design studies. See, for example: Singharoy A, Sereda Y V, Ortoleva P J. Hierarchical Order Parameters for Macromolecular Assembly Simulations I: Construction and Dynamical Properties of Order Parameters. accepted to J Chem Theor Comput. 2012; and, Singharoy A, Cheluvaraja S, Ortoleva P J. Order parameters for macromolecules: Application to multiscale simulation. J Chem Phys. 2011; 134:044104.

Figure 2:
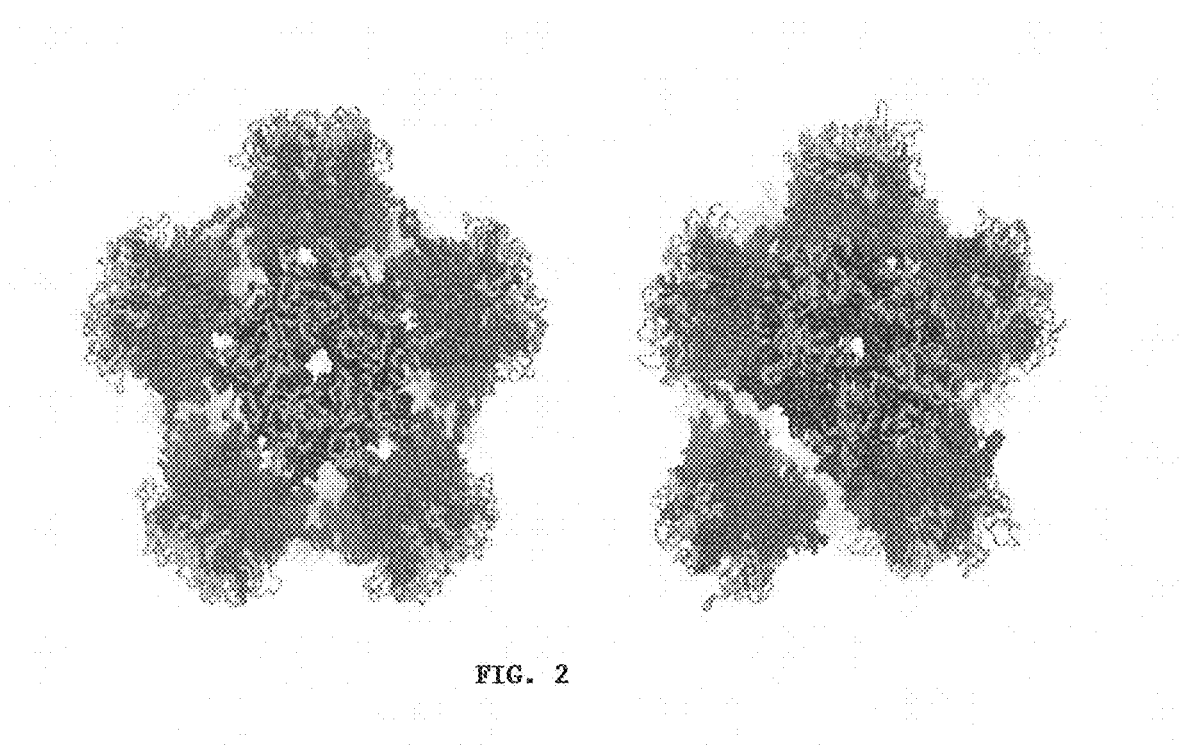
FIG. 2 illustrates DMS-predicted evolution of the HPV VLP in an aqueous environment at 300 K, pH 7, salinity 0.25 M NaCl, with the starting structure on the left and the structure after 200 ns simulation on the right. This computationally predicted instability of VLP agrees with experimental observation that such truncated monomers fail to form VLPs, while a non-truncated system remains intact once assembled.
Figure 3:
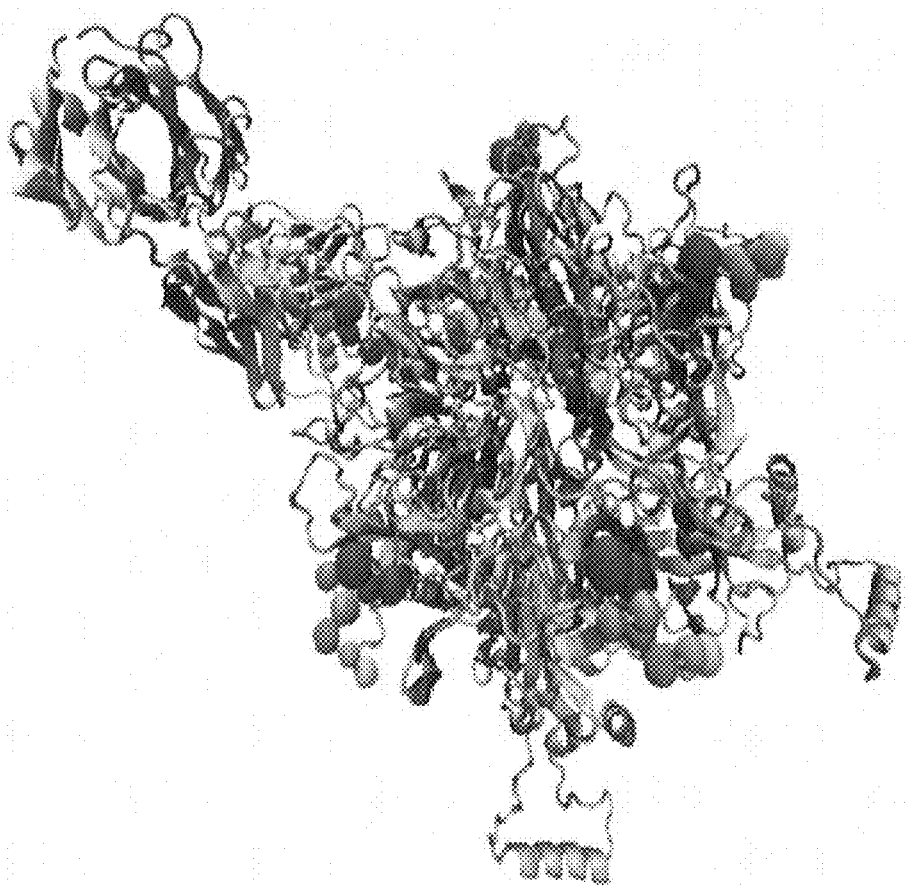
FIG. 3 illustrates an HPV 16 L1 pentamer (grey) wherein epitopes of hepatitis B virus (hereinafter sometimes HBV) are inserted computationally in place of EF loops of L1 monomer (sphere representation). The purple cartoon shows the antibody for HBV docked computationally near this engineered epitope as the starting point of a DMS simulation to provide antibody binding energy as one of the molecular metrics used.

DMS simulator is significant to this computer-aided vaccine design strategy. Its accuracy has been previously validated via a number of applications. These include polyalanine folding from a linear to a globular state (see, for example, Jaqaman K, Ortoleva P J. New space warping method for the simulation of large-scale macromolecular conformational changes. J Comput Chem. 2002; 23(4):484-91), self-assembly of nanocomponents into composites (see, for example, Pankavich S, Shreif Z, Miao Y, Ortoleva P J. Self-assembly of nanocomponents into composite structures: Derivation and simulation of Langevin equations J Chem Phys. 2009; 130(19):194115-24), nucleation and front propagation pathways in virus capsid structural transition (see, for example: Miao Y, Ortoleva P J. Viral structural transitions: an all-atom multiscale theory. J Chem Phys. 2006; 125(21):214901; and, Miao Y, Johnson J E, Ortoleva P J. All-Atom Multiscale Simulation of Cowpea Chlorotic Mottle Virus Capsid Swelling. J Phys Chem B. 2010; 114(34):11181-95), counter-ion induced collapse in viral RNA and stability of RNA-protein complexes (see, for example, Singharoy A, Cheluvaraja S, Ortoleva P J. Order parameters for macromolecules: Application to multiscale simulation. J Chem Phys. 2011; 134:044104), and disassembly and conformational fluctuations of T=1 HPV VLP (FIG. 2).

Another aspect of VLP design addressed by this approach is VLP thermal stability. For example, if the C-terminal helices of the L1 protein are removed, laboratory experiments show that the VLP does not self-assemble. See, for example, Bishop B, Dasgupta J, Chen X. Structure-based engineering of papillomavirus major capsid L1: controlling particle assembly. Virology J. 2007; 4:3. This is predicted via DMS simulation (FIG. 2). See, for example, Singharoy A, Cheluvaraja C, Joshi H, McWillaims K, Brown D, Ortoleva P J. Simulating the Self-assembly and Stability of VLP-type Vaccines: Application to Human Papillomavirus. In preparation. 2010. When the helices are present, DMS predicts that the structure is stable, as observed. See, for example, Bishop B, Dasgupta J, Chen X. Structure-based engineering of papillomavirus major capsid L1: controlling particle assembly. Virology J. 2007; 4:3. This illustrates the utility of DMS to design stable VLP for given sequence and microenvironmental conditions.

§II. B Immunogenicity Prediction

There is currently a large gap between predicting VLP configuration and its evolution in time, versus predicting the antibody response of the immune system. The present invention addresses this gap as follows. The molecular and VLP-wide factors predicted via DMS simulations are used as input to a formula relating them to immunogenicity. This formula is calibrated using the developed database on the structure and immunogenicity of a spectrum of VLPs. DMS output contains information on VLP structural stability and detailed molecular metrics including epitope structure, fluctuations, and the strength of binding to antibodies. Strength of binding to antibodies is itself believed to be an indicator of immunogenicity. See, for example, Joshi H, Lewis K., Singharoy A, Ortoleva P J. Computational Epitope Engineering: efficient simulation approach to VLP-based vaccine design. in preparation. 2012. For example, the disclosed "epitope fluctuation—immunogenicity hypothesis" suggests that for similar immunogenicity in the L1 pentamer and VLP to be realized, epitopes in the designed VLP must have the same low level of fluctuations as for the epitopes in the immunogenic icosahedral VLP.

The highly efficient all-atom simulations of VLPs, informatics based immunogenicity scoring, and shortlisting of VLP candidates as likely vaccine makes VCAD a highly useful computer-aided design platform. The shortlist thus developed serves to minimize the laboratory vaccine design expense and time.

§II. C VLP Designs

A set of candidate vaccine VLPs is designed based on novel structures whose immunogenicity is tested via VCAD and associated molecular-scale properties. Proposed VLPs are thermochemically stable, and have epitope behavior mimicking that of the target virus. Two types of VLPs included in the analysis are based on FDA approved nanoparticles. The first is a VLP that is a successful vaccine for one virus but with epitopes replaced by those of the target virus. The second is a readily synthesized inert nanocore dressed with epitope-bearing components of the target virus. Since the central elements of these two deigns are FDA-approved nanoparticles, major cost savings are expected via the repeated use of similar platforms.

§III Overview

Efficiencies in vaccine discovery are achieved via a novel computer-aided VLP design strategy. This strategy mirrors that of conventional laboratory approaches. However, here, VLPs are computationally synthesized. The stability and immunogenicity of the thus synthesized VLPs are probed via the all-atom physics that underlies DMS simulations. Two key elements of the VCAD approach are developed and validated: connecting molecular scale metrics to immunogenicity via a bio informatics; and, constructing VLPs computationally and predicting their immunogenicity.

§III. A Construct and Populate the VCAD Database Used to Calibrate the Immunogenicity Prediction Formula A database is constructed that archives experimental and computationally derived information on a variety of viruses and associated VLPs. This information includes structure, molecular metrics, and observed degrees of immunogenicity. To populate the database, for each of a variety of VLPs, DMS is run to obtain quantitative information on the molecular metrics of each of the variety of VLPs. A DMS simulation is automatically analyzed to extract the molecular scale metrics via a computer program written in the python scripting language available from www.python.org.

The VCAD database is implemented via the relational database software MYSQL available from: www.mysql.com. For each pathogen and VLP, this database archives: structural data for the VLP or virus; structural data for the antibody; values of multiple molecular metrics obtained via DMS simulation; experimental information on immunogenicity; annotation on sources of information provided; and DMS input files used to probe thermal stability or molecular metrics. For a preliminary version of VCAD used to demonstrate the described approach, VLPs related to HPV, poliovirus, and hepatitis E virus (hereinafter sometimes HEV) are used. FIG. 2 illustrates the DMS-predicted evolution. The starting structure of the HPV VLP in an aqueous environment at 300 K, pH 7, salinity 0.25 M NaCl is on the left. The simulated structure after 200 ns of evolution is on the right. This computationally predicted instability of VLP agrees with the experimental observation that such truncated monomers fail to form VLPs, while the non-truncated system (not shown) remains intact once assembled.

§III. B Calibrate and Validate the Immunogenicity-Prediction Formula Using Information in the VCAD Database Immunogenicity Scoring While it is commonly thought that epitope structure plays a predominant role in VLP immunogenicity, other factors may also be relevant. Including several of them in the analysis adds additional reliability in immunogenicity prediction. Such molecular metrics include: (1) overall VLP size and shape; (2) thermal stability in blood or other fluids; (3) epitope peptide sequence; (4) epitope 3-dimensional conformation; (5) structures of a set of closely lying epitopes relative to each other; (6) amplitude of epitope structural fluctuations (see, for example, Joshi H, Cheluvaraja S, Somogyi E, Brown D R, Ortoleva P J. A molecular dynamics study of loop fluctuation in human papillomavirus type 16 virus-like particles: a possible indicator of immunogenicity. Vaccine. 2011; 29(51):9423-30); and, (7) strength of epitope binding to an antibody for the target virus. See, for example, Joshi H, Lewis K, Singharoy A, Ortoleva P J. Computational Epitope Engineering: efficient simulation approach to VLP-based vaccine design. in preparation. 2012. These metrics are connected to immunogenicity as follows.

The DMS simulator predicts the timecourse of the positions and momenta of all atoms in the VLP and its microenvironment. From this, M molecular metrics such as the seven above (M=7) are constructed. Let $\lambda_m$ be the mth metric (m=1, 2, ... M). Each $\lambda_m$ is defined to be positive and is such that high immunogenicity is indicated when it is small. For example, $\lambda_1$ is the time-average of the fluctuation of epitope atom positions, $\lambda_2$ is the average difference between atomic positions in the VLP versus on the virus, and $\lambda_3$ is the inverse of the energy of binding of an antibody to an epitope. Next the mth immunogenicity factor $\mu_m$ is defined such that $\mu_m=(1+x_m)^{-1}$ where $x_m=(a_m\lambda_m)^2$ for factor $a_m$ to be calibrated. From this expression, $\mu_m$ near zero implies low likely immunogenicity, and conversely, $\mu_m$ near 1 implies high likely immunogenicity. If $\lambda_m$ is near $a_m^{-1}$ then $\mu_m$ is near ½ so that marginal immunogenicity is indicated. From the M immunogenicity metrics $\{\mu_1, \mu_2, \ldots \mu_M\}$ an average value $\mu$ is constructed for a candidate VLP. Let $w_m$ be a weight that expresses the expectation that, regardless of which VLP, a factor $\lambda_m$ is important relative to others. Then the immunogenicity based on all the metrics is taken to be a $w_m$-weighted average of $\mu_m$. However, for a given VLP all the metrics may not be available (e.g., if no antibody structure for the given virus is known). With this, the expected immunogenicity $\mu$ for a given VLP is taken to be $$\mu=(\Sigma^* w_m)^{-1}\Sigma^* w_m\mu_m,$$

summing over all m, except that the * (asterisks) on the $\Sigma$s indicate that only contributions for metrics that are available are included.

Calibration of the Immunogenicity Law

Let $\underline{a}=\{a_1, a_2, \ldots a_M\}$, and similarly for $\underline{w}$ and $\underline{\lambda}$. The $\underline{a}$ and $\underline{w}$ factors are calibrated using standard least squares fitting techniques. See, for example, Press W H, Flannery B P, Teukolsky S A, Vetterling W T. Numerical Recipes: The Art of Scientific Computing. Cambridge: Cambridge U. Press; 1987. This formulation allows for the use of a heterogeneous database (i.e., it works even when all the $\lambda_m$ are not available for all VLPs in the database).

Validation

Validation of the immunogenicity formula is accomplished via a standard statistical approach. The database of VLPs with experimentally known immunogenicity are randomly divided into two groups. One is the "database" and the other is the "predictions" for a set of VLPs of interest. By comparing the "predicted" and "observed" immunogenicities, a percent success in predicting immunogenicity is computed. This procedure is repeated several times with different random divisions of the data to obtain an estimate of overall success. If the result is not adequate, other immunogenicity formulas are developed and the database is expanded. Adequacy of the database is indicated when further addition of new VLPs does not substantially change $\underline{a}$ and $\underline{w}$.

Ultimately, the immunogenicity $\mu$ is related to a quantitative laboratory measure such as observed antibody counts. This enables a more quantitative calibration of the $\underline{a}$-dependence of $\mu(\underline{\lambda}, \underline{a})$.

§III. C Validation of Immunogenicity Prediction Approach Using Data on HPV, Poliovirus, and Hepatitis E The application of the described VCAD approach for two VLP designs is demonstrated. For each demonstration, the VLP is generated computationally, simulated via the DMS software, and the simulated information is then used to predict its immunogenicity for a target virus. This validation proceeds as follows.

§III. C. 1 Engineering Epitopes of a Target Virus on the HPV VLP

Vaccines against numerous human pathogens are not available. What if the HPV VLP could be used to induce an immune response against non-HPV pathogens by including epitopes of these pathogens within the L1 amino acid sequence? In this way, HPV VLPs are used as the delivery system for epitopes of a target virus. Sadeyen et al., reported results on the insertion of a foreign amino acid sequence into HPV 16 epitope loops. See, for example, Sadeyen J-Ré, Tourne S, Shkreli M, Sizaret P-Y, Coursaget P. Insertion of a foreign sequence on capsid surface loops of human papillomavirus type 16 virus-like particles reduces their capacity to induce neutralizing antibodies and delineates a conformational neutralizing epitope. Virology. 2003; 309(1):32-40. Sadeyen et al., found the introduction of a foreign sequence reduced the immunological response to the HPV epitope. The hepatitis B core antigen (HBc) that was introduced, however, did elicit the formation of antibodies. This suggests a possibility of using HPV capsids as a platform for the development of vaccines against other viruses.

The starting point for this exercise is the atom-resolved T=1 or 7 structure of HPV. HBV epitope is computationally inserted to replace the EF loop of HPV. This replacement is based on the sequence alignment of the HPV loop and the epitope of HBV to conserve overall charge using, for example, EMBOSS sequence alignment tool. See, for example, Rice P, Longden I, Bleasby A. EMBOSS: The European Molecular Biology Open Software Suite. Trends in Genet. 2000; 16(6):276-7). It also eliminates one of the most immunogenic HPV epitopes, thereby making the design less sensitive to HPV antibodies. The antibody for HBV (see, for example, Chi S-W, Maeng C-Y, Kim S J, Oh M S, Ryu C J, Kim S-J, et al. Broadly neutralizing anti-hepatitis B virus antibody reveals a complementarity determining region H3 lid-opening mechanism. Proc Natl Acad Sci. 2007; 104:9230-5) is docked computationally on the inserted epitope. DMS simulation of this system yields the binding energy as one of the molecular metrics used in the immunogenicity analysis.

§III. C. 2 Epitope Dressed Nanocores

Figure 4:
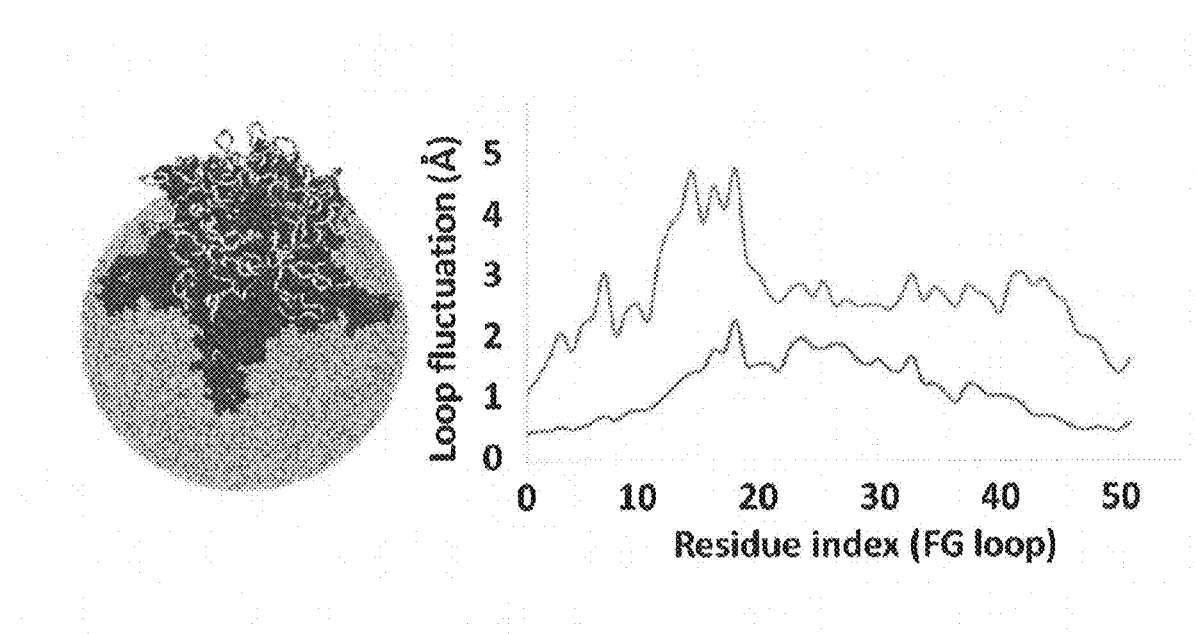
FIG. 4 illustrates a silica nanoparticle, illustrated in yellow and red spheres, used as a platform to present pentameric HPV structures, illustrated in blue, or directly the epitopes, illustrated in pink, of a target virus. The reduction in epitope fluctuation, illustrated on the right, for this construct relative to that of the free pentamer suggests this structure as an attractive candidate for a cost-effective vaccine VLP.

Synthetic vaccine nano-particles are designed by binding epitope bearing proteins of a target virus to FDA approved silica nanocores (hereinafter sometimes NCs). Amorphous silica NCs with "isolated" or "viscinal" silanol surfaces are prepared via simulated annealing of crystalline silica using BKS and CHARMM type force fields. See, for example, Cruz-Chu E R, Aksimentiev A, Schulten K. Water-Silica Force Field for Simulating Nanodevices. The Journal of Physical Chemistry B. 2006; 110(43):21497-508. This is readily achieved computationally using VMD and NAMD. See, for example: Humphrey W, Dalke A, Schulten K. VMD: Visual molecular dynamics. J Mol Graph. 1996; 14(1):33-8; and, Phillips J C, Braun R, Wang W, Gumbart J, Tajkhorshid E, Villa E, et al. Scalable molecular dynamics with NAMD. J Comput Chem. 2005; 26(16):1781-802. Covalent attachment between the L1 protein and silica surface achieved via $-(CH_2)_nNH_2$ linkers provides thermostability to these structures and minimizes epitope fluctuation. See FIG. 4.

Constructing an accurate computer model of inorganic NCs dressed with viral proteins requires an accurate interatomic force field. This force field quantifies the interaction of the epitope-bearing proteins with silica nanoparticles on which they are mounted. Force fields are not available for the molecules that link the silica NCs to the epitope-bearing viral proteins. These force fields are developed by first carrying out high-level quantum chemical calculations on model systems consisting of a relatively small moiety representing the NC, a $-(CH_2)_3NH_2$ linker molecule, and a small section of viral protein. Development begins with a very simple silica surface model, FIG. 4. The linker molecule is parametrized. The complexity of the model is then increased while monitoring the changes of the force fields for convergence to a uniform value. These quantum calculations allow for estimating the forces within the small model, which is tested and refined against quantum chemical data and experimental observables. This task requires substantial expertise in electronic structure calculations to distinguish spurious artifacts from important electronic effects.

Consider surface functionalization of amorphous silica with $-(CH_2)_nNH_2$ linkers and attachment of L1 pentamers. Several factors that control epitope structure and fluctuations (implying nanostructure immunogenicity) are explored, for example, linker length, mass of the inert NC, surface curvature and concentration of surface silanols. Linker length is controlled by choosing the number of $-CH_2-$ groups in the aliphatic chain. System mass is limited by the size of the NC. Surface concentration of silanol is controlled by randomly breaking siloxane bonds and hydroxyl capping the surface dangling atoms using surface generation protocols. See, for example, Aksimentiev A, Brunner R, Cohen J, corner J, Cruz-Chu E R, Hardy D, et al. Computer Modeling in Biotechnology. A Partner in Development. Nanostructure Design Methods in Molecular Biology: SpringerLink; 2008. p. 181-234. DMS is used to simulate the stability and molecular-scale characteristics of the above NC-based constructs. This yields an assessment of the similarity of the molecular-scale metrics for NC-based vaccine nanoparticles versus, for example, the T=7 HPV VLP. These simulations are repeated with epitopes of other viruses (notably poliovirus and Hepatitis E), with silica NCs as the delivery system. Preliminary results from the simulations of these designs demonstrate their thermal stability and low epitope fluctuations. See FIG. 4. Thus, such VLPs are used as input to DMS to predict their stability and molecular-scale metrics. The latter are used for immunogenicity prediction.

IV. Another Embodiment

The high specificity of the neutralizing antibody response of the immune system to virus type suggests that there is a relationship between molecular-scale properties of a virus surface and the immune response. This correlation indicates that one could define the immunogenicity of a candidate vaccine nanoparticle as a measure $\mu$, which would depend on the molecular-scale properties of the virus surface (here, denoted molecular metrics). This immunogenicity metric-relationship is explored.

Figure 5:
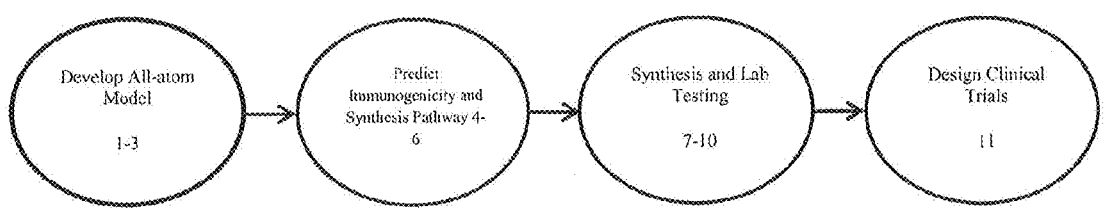
FIG. 5 illustrates a highly simplified flow diagram of a DMS simulation.

This computer-aided design approach starts with an all-atom structure of a VLP that is the putative active ingredient in the vaccine. This structure is then used as input to DMS. DMS is a simulation package designed for modeling viruses, VLPs, and other many-atom systems with great efficiency and accuracy. Somogyi, A., A. AbiMansour, and P. J. Ortoleva, *DMS: A multiscale molecular simulator*. In preparation. The molecular-scale properties that result from these simulations are used to predict immunogenicity via an informatics approach. VLPs with high predicted immunogenicity can then be synthesized and subjected to traditional laboratory immunogenicity testing. This computer-aided vaccine discovery workflow is summarized in FIG. 5.

While epitope structure has been proposed as a predominant factor in VLP immunogenicity, consideration of other metrics could improve the reliability of immunogenicity prediction. Possible molecular metrics to be included in the analysis are as follows: (a) overall VLP size and shape; (b) VLP thermal stability in blood or other fluids; (c) epitope peptide sequence; (d) average epitope 3-D conformation; (e) structures of sets of closely lying epitopes relative to each other; (f) amplitude of epitope structural fluctuations, Joshi, H., S. Cheluvaraja, E. Somogyi, D. R. Brown, and P. J. Ortoleva, *A molecular dynamics study of loop fluctuation in human papillomavirus type 16 virus-like particles: a possible indicator of immunogenicity*. Vaccine, 2011. 29(51): p. 9423-9430; (g) solvent accessibility of the epitope; and (h) strength of antibody binding to the epitope of the target virus as presented by the VLP, Joshi, H., K. Lewis, A. Singharoy, and P. J. Ortoleva, *Computational Epitope Engineering: efficient simulation approach to VLP-based vaccine design*. in preparation, 2012. In the present approach, such metrics are used to generate a quantitative formula for assessing immunogenicity.

The bioinformatics methodology included as a step in the vaccine discovery workflow (FIG. 5) utilizes the Vaccine Computer-Aided Design database (VCAD) of information on nanoparticles with experimentally known immunogenicity ruby.chem.indiana.edu/~scorenfl/vaccineDB/vlp.php). VCAD is briefly described (Sect. V.B). *VLP Immunogenicity*

*Database*, 2012: In Preparation. The development, calibration, and validation of the immunogenicity formula are presented (Sect. V.C-E).

V. Methods and Materials

V. A Epitope Structural Metrics

Specific molecular metrics for a spectrum of VLPs are provided in the VCAD database as follows.

Loop Fluctuation Index

Overall epitope structural fluctuation is used as a molecular metric. This entity is not easily quantified in X-ray or cryo-EM data. While a structure provides the most likely or average configuration, its fluctuation measures the importance of other configurations away from the average, but which may (according to our immunogenicity hypothesis; Joshi, H., S. Cheluvaraja, A. Somogyi, D. R. Brown, and P. J. Ortoleva, *Role of Epitope Fluctuation in Immunogenicity: A Molecular Simulations Study of Human Papillomavirus. Vaccine*, 2011. 29(51): p. 9423-9430) be functionally relevant. Dynamic information obtained from MD provides advantages over the inherently averaged experimental data. Positional variance is computed by summing the RMS deviation of individual backbone atom positions and dividing by the number of backbone atoms in the loop. This measure is slightly different from the usual root mean square fluctuation (RMSF). RMSF measures fluctuation from a fixed reference structure by aligning two structures, thus eliminating translational and rotational motions. In contrast, average loop positional variance calculated here contains contributions from overall displacements of the loops and their motions relative to the rotation/translation and internal motions of the assembly. The overall motions potentially affect epitope location and orientation within loops; according to our hypothesis, the overall fluctuations also affect immunogenicity and binding properties of the monomer or larger assembly. Thus, including the effect of overall and internal assembly motions on loop fluctuations provides a more complete measure of their potential relevance to immunogenicity. Positional variance or fluctuation index for a residue i is calculated as follows:

$$F_i = \sum_{t=0}^{T} \sqrt{\langle (x - \langle x \rangle)^2 \rangle} \quad (1)$$

The fluctuation index for the entire loop is an average of individual residue fluctuations.

Dihedral Distribution

Distribution of backbone dihedral angles for the epitope-bearing loop is measured to compare how the epitope-containing loops span the configurational space. This quantity complements fluctuation index. Loops with greater fluctuation index indicate higher flexibility and would span more configurational space compared to those with lower flexibility. Backbone dihedral angles are defined as in FIG. 6.

Sequence Similarity

When VLP structures for various strains of a virus are known, loops containing the same epitope may differ in sequence due to mutation. This situation may also arise if a mutation is introduced to achieve a given VLP functionality. In such cases, a wild type protein loop can be used for comparison to quantify the notion of sequence similarity. In particular, the molecular metrics used in this context are the similarity index from pair-wise or multiple sequence alignment. Mount, D. W., *Bioinformatics: Sequence and Genome Analysis* 2001, New York: Cold Spring Harbor Laboratory Press. In our script, this is achieved using EMBOSS utility. *Bioinformatics tools from European Bioinformatics Institute (EMBL-EBI).*

Antibody—Epitope Binding Affinity

The energy of binding between epitope and antibody is used as an immunogenicity metric. This binding energy indicates some structural compatibility that would be a measure of immunogenicity (i.e., an antibody expressed by the immune system to the target virus would interact strongly with a loop on the VLP of interest if it mimicked the structural properties of the target virus). This is computed using standard analysis tools available from GROMACS (Berendsen, H. J. C., D. van der Spoel, and R. van Drunen, *GROMACS: A message-passing parallel molecular dynamics implementation.* Comput. Phys. Commun., 1995. 91(1-3): p. 43-56; Lindahl, E., B. Hess, and D.v.d. Spoel, *GROMACS 3.0: A package for molecular simulation and trajectory analysis.* J. Mol. Mod., 2001.7: p. 306-317) or NAMD (Phillips, J., R. Braun, W. Wang, J. Gumbart, E. Tajkhorshid, E. Villa, C. Chipot, R. Skeel, L. Kale, and K. Schulten, *Scalable molecular dynamics with NAMD.* J Comput Chem, 2005. 26(16): p. 1781-1802) package that are accessed from our Python script. The binding affinity of the aforementioned pairs is also evaluated using VMD (Humphrey, W., A. Dalke, and K. Schulten, *VMD: Visual molecular dynamics.* J. Mol. Graph., 1996. 14(1): p. 33-38) and NAMD. An antibody-epitope complex is immersed in a solvated system. Therefore, the following equation is used to calculate the average binding affinity.

$$(E_{total} - E_{water+ion}) - (E_{antibody+water+ion} + E_{pentamer+water+ion}) = \text{Binding Affinity} \quad (2)$$

Solvent Accessible Surface Area

Binding of an antibody is impacted mainly by the degree of exposure of the epitope-containing loop to the solvent. Thus "solvent accessible surface area" (SASA) is computed as a measure of molecular metric of immunogenicity. Since its first definition by Lee and Richards (Lee, B. and F. M. Richards, *The interpretation of protein structures: estimation of static accessibility.* J Mol Biol, 1971. 55(3): p. 379-400) there have been many algorithms to compute SASA. Shrake, A. and J. A. Rupley, *Environment and exposure to solvent of protein atoms. Lysozyme and insulin.* Journal of Molecular Biology, 1973. 79(2): p. 351-371; Weiser, J., P. Shenkin, and W. Still, *Approximate atomic surfaces form linear combinations of pairwise overlaps (LCPO).* Journal of Computational Chemistry, 1999. 20(2): p. 217-230; Klenin, K., F. Tristram, T. Strunk, and W. Wenzel, *Derivatives of molecular surface area and volume: Simple and exact analytical formulas.* Journal of Computational Chemistry, 2011. 32(12): p. 2647-2653. Here, and in common usage, it is calculated via the 'rolling ball' algorithm; a sphere (of solvent) of a particular radius is used to probe the surface of the molecule based on the particular implementation as in GROMACS. In particular, g_sas, Eisenhaber, F., P. Lijnzaad, P. Argos, C. Sander, and M. Scharf, *The double cubic lattice method: Efficient approaches to numerical integration of surface area and volume and to dot surface contouring of molecular assemblies.* Journal of Computational Chemistry, 1995. 16(3): p. 273-284, is used in our Python script to compute SASA.

V. B The VCAD Database

To train the computer-aided vaccine design method, the VCAD database was constructed to archive experimentally derived information on a variety of viruses and VLPs. To populate VCAD with quantitative data, the bionanosystem simulator DMS was run to obtain molecular metrics for each VLP.

The VCAD database was implemented in MYSQL. *MYSQL*. 2013 [cited 2013; Available from: www.mysql.com. The following information is archived for each pathogen and VLP: (a) structural data for the VLP or virus; (b) structural data for the antibody; (c) values of multiple molecular metrics as defined in Sect. II.A and obtained via DMS simulation; (d) experimental information on immunogenicity; (e) annotation on sources of information; and (f) DMS input files used to extract molecular metrics. Presently, VCAD includes VLPs related to human papillomavirus (HPV) (Chen, X. S., R. L. Garcea, I. Goldberg, G. Casini, and S. C. Harrison, *Structure of Small Virus-like Particles Assembled from the L1 Protein of Human Papillomavirus 16*. Mol. Cell, 2000. 5(3): p. 557-567), poliovirus (Miller, S. T., J. M. Hogle, and D. J. Filman, *Ab initio phasing of high-symmetry macromolecular complexes: successful phasing of authentic poliovirus data to 3.0 Å resolution*. J. Mol. Biol., 2001. 307(2): p. 499-512; Lentz, K., A. Smith, S. Geisler, S. Cox, P. Buontempo, A. Skelton, J. DeMartino, E. Rozhon, J. Schwartz, V. Girijavallabhan, J. O'Connell, and E. Arnold, *Structure of poliovirus type 2 Lansing complexed with antiviral agent SCH48973: comparison of the structural and biological properties of three poliovirus serotypes*. Structure, 1997. 5(7): p. 961-978; and, Grant, R. A., C. N. Hiremath, D. J. Filman, R. Syed, K. Andries, and J. M. Hogle, *Structures of poliovirus complexes with anti-viral drugs: implications for viral stability and drug design*. Curr. Biol., 1994. 4(9): p. 784-797), enterovirus (Wang, X., W. Peng, J. Ren, Z. Hu, J. Xu, Z. Lou, X. Li, W. Yin, X. Shen, C. Porta, T. S. Walter, G. Evans, D. Axford, R. Owen, D. J. Rowlands, J. Wang, D. I. Stuart, E. E. Fry, and Z. Rao, *A sensor-adaptor mechanism for enterovirus uncoating from structures of EV71*. Nat. Struct. Mol. Biol., 2012. 19(4): p. 424-429), and hepatitis E virus (HEV) (Guu, T. S. Y., Z. Liu, Q. Ye, D. A. Mata, K. Li, C. Yin, J. Zhang, and Y. J. Tao, *Structure of the hepatitis E virus-like particle suggests mechanisms for virus assembly and receptor binding*. Proc. Nat. Acad. Sci., 2009. 106(31): p. 12992-12997).

V. C The Immunogenicity Formula

A formula used for predicting the immunogenicity of a VLP based on simulated molecular metrics is as follows. First, define $\mu^{l,obs}$ to be the observed immunogenicity of VLP l and $\mu^{l,pre}$ to be its predicted immunogenicity where l=1, 2, ... $N_{VLP}$, where $N_{VLP}$ is the total number of VLPs used in the analysis. The convention is that $0 \leq \mu^{l,obs} \leq 1$. Due to the typically qualitative nature of immunogenicity data, semi-quantitative information was archived from publications (see citations in the sobs VCAD database) in the following manner: $\mu^{l,obs}$:0.001 (essentially not immunogenic), 0.25 (very weakly immunogenic), 0.5 (weakly immunogenic), 0.75 (immunogenic), and 0.99 (strongly immunogenic). Thus, $\mu^{l,obs}$ near zero implies low observed immunogenicity.

Next, define the immunogenicity $\mu^l_m$ for the lth VLP implied by the mth metric to be $$\mu^l_m = (1 + (a_m + \lambda^l_m)^2)^{-1} \quad (3)$$

Let m=1, 2, ... M, where M is the number of molecular metric types derived from simulation of a VLP, and used in the analysis. For the metrics defined in Sect. II.A, M=5. In the formula above, $a_m$ is a factor to be calibrated and $\lambda^l_m$ is the positive-valued, computationally-derived mth metric for VLP l. For example, for VLP l, $\lambda^l_1$ could be the time-average of the fluctuation of epitope atom positions (Joshi, H., S. Cheluvaraja, A. Somogyi, D. R. Brown, and P. J. Ortoleva, *Role of Epitope Fluctuation in Immunogenicity: A Molecular Simulations Study of Human Papillomavirus*. Vaccine, 2011. 29(51): p. 9423-9430), $\lambda^l_2$ could be the RMS average difference between atomic positions in the VLP versus on the virus, and $\lambda^l_3$ could be the inverse of the energy of binding of an antibody to an epitope presented on the surface of the VLP. From traditional immunology, small values of these quantities are expected to indicate high immunogenicity. Thus, high immunogenicity is indicated when $\lambda^l_m$ is small, and weak immunogenicity is indicated when $\lambda^l_m$ is near $a_m^-$. Equation 3 has this behavior.

V. D Calibration of the Immunogenicity Formula

A component of the present analysis is the development of a measure for the reliability of a given metric in immunogenicity prediction. Let $w_m$ be a measure of the degree to which metric m is a reliable indicator of immunogenicity. In particular, the predicted immunogenicity for VLP l is defined via $$\mu^{l,pre} = \sum_m {}^{(l)}w_m \mu^l_m \Big/ \sum_{m'} {}^{(l)}w_{m'} \quad (4)$$

An element of the analysis is the construction of the weights $w_m$ using the database (see below). The structure of this formula accounts for the complexity that not all metrics may be available for all VLPs (e.g., if no antibody structure for the given virus is known). Thus, (l) on an m sum indicates that m accounts for only the $\lambda^l_m$ of VLP l for which data is available.

A measure of error between predicted $\mu^{l,pre}$ and observed $\mu^{l,obs}$ immunogenicity (where observed immunogenicity values are taken from the VCAD database) serves as the basis of calibration. Let the error in predicted versus observed immunogenicity be defined as follows:

$$\text{ERROR}(\underline{a}, \underline{w}) = \sum_{l=1}^{N_{VLP}} (\mu^{l,obs} - \mu^{l,pre})^2. \quad (5)$$

With this, the error depends on the calibration factors $\underline{a}$ and $\underline{w}$, where $\underline{a} = \{a_1, a_2, \ldots a_M\}$ and $\underline{w} = \{w_1, w_2, w_M\}$. For normalization, $w_1 + w_2 + \ldots + w_M = 1$. By minimizing ERROR with respect to $\underline{a}$ and $\underline{w}$, the immunogenicity formula is calibrated. The minimization of ERROR is obtained through use of SciPy software, Jones, E., T. Oliphant, and P. Peterson, *SciPy: Open Source Scientific Tools for Python*, 2001, specifically the sequential least squares (SLSQP) and simulated annealing algorithms, Press, W. H., B. P. Flannery, S. A. Teukolsky, and W. T. Vetterling, *Numerical Recipes: The Art of Scientific Computing*. 1987, Cambridge: Cambridge U. Press.

V. E Validation of the Immunogenicity Formula

Validation of the immunogenicity formula is accomplished via a standard binning statistical approach, Cowan, G., *Statistical Data Analysis*, 1998, Oxford University Press New York. The database of VLPs with experimentally known immunogenicities is divided into two groups at random. One is treated as "database" and the other as "predictions" for the former set VLPs. By comparing the "predicted" and "observed" immunogenicities, a percent success in predicting immunogenicity is computed. This procedure is repeated with different random divisions of the data to obtain an estimate of overall success. Adequacy of the database is indicated when the calibrated values $\underline{a}$ and $\underline{w}$ do not substantially change with addition of new VLPs.

A second statistical assessment of the viability of the molecular metrics is as follows. All VLPs in the database are paired such that the observed immunogenicities between partners differ by less than 0.05. Then, if a given molecular metric is a reliable indicator of immunogenicity, a plot of points in the plane of a given molecular metric for one VLP versus that of the other in a pair should lie close to a 45° line. If the plot is scattered then the given metric is not reliable. This correlation analysis is carried out for all the molecular metrics used.

The disclosures of all of the references cited herein are hereby incorporated by reference.

What is claimed is:

1. A method for the computer-aided design of vaccines, the method comprising performing a molecular simulation of a proposed vaccine nanoparticle on a computer to predict the proposed vaccine nanoparticle's overall and molecular scale properties, determining a contribution to immunogenicity for each of the molecular scale properties based on a database that pairs experimentally predetermined immunogenicity to computationally predetermined molecular scale properties for each of a plurality of vaccine nanoparticles of known immunogenicity to predict the likely immunogenicity of the proposed vaccine nanoparticle, and synthesizing the proposed vaccine nanoparticle when the proposed vaccine nanoparticle is predicted to be immunogenic.

2. The method of claim 1 wherein the proposed vaccine nanoparticle's overall and molecular scale properties include overall size, geometry and thermal stability of the proposed vaccine nanoparticle.

3. The method of claim 1 wherein the proposed vaccine nanoparticle's overall and molecular scale properties include epitope conformation, the geometric relation between multiple closely-lying epitopes, and the statistics of the variations of epitope structure over time as predicted by the molecular simulation.

4. The method of claim 1 wherein using molecular simulation comprises using a deductive multiscale simulator (DMS) simulation.

5. A method for the computer-aided design of vaccines, the method comprising performing a molecular simulation of a proposed vaccine nanoparticle on a computer to predict the proposed vaccine nanoparticle's overall and molecular scale properties, determining a contribution to immunogenicity for each of the molecular scale properties based on a database that pairs experimentally predetermined immunogenicity to computationally predetermined molecular scale properties for each of a plurality of vaccine nanoparticles of known immunogenicity to predict the likely immunogenicity of the proposed vaccine nanoparticle, and synthesizing the proposed vaccine nanoparticle and experimentally measuring the immunogenicity of the proposed vaccine nanoparticle when the likely immunogenicity ($\mu$) is 0.75 or greater.

6. The method of claim 5 wherein the experimentally measuring step comprises experimentally measuring antibody binding strength.

7. The method of claim 5 wherein the proposed vaccine nanoparticle's overall and molecular scale properties include overall size, geometry and thermal stability of the proposed vaccine nanoparticle.

8. The method of claim 5 wherein the proposed vaccine nanoparticle's overall and molecular scale properties include epitope conformation, the geometric relation between multiple closely-lying epitopes, and the statistics of the variations of epitope structure over time as predicted by the molecular simulation.

9. The method of claim 5 wherein using molecular simulation comprises using a deductive multiscale simulator (DMS) simulation.

* * * * *